US012377059B2

(12) United States Patent
Madhavamenon et al.

(10) Patent No.: US 12,377,059 B2
(45) Date of Patent: Aug. 5, 2025

(54) COMPLEXES COMPRISING COLLAGEN PEPTIDES AND CURCUMINOIDS AND COMPOSITIONS THEREOF

(71) Applicant: AKAY NATURAL INGREDIENTS PRIVATED LIMITED, Cochin (IN)

(72) Inventors: Krishnakumar Illathu Madhavamenon, Kerala (IN); Balu Paulose Maliakel, Kerala (IN)

(73) Assignee: AKAY NATURAL INGREDIENTS PRIVATE LIMITED, Cochin (IN)

( * ) Notice: Subject to any disclaimer, the term of this patent is extended or adjusted under 35 U.S.C. 154(b) by 0 days.

(21) Appl. No.: 18/353,251

(22) Filed: Jul. 17, 2023

(65) Prior Publication Data

US 2024/0050381 A1 Feb. 15, 2024

Related U.S. Application Data

(63) Continuation of application No. 16/773,494, filed on Jan. 27, 2020, now abandoned.

(30) Foreign Application Priority Data

Jan. 28, 2019 (IN) .............................. 201941003319

(51) Int. Cl.
*A61K 31/12* (2006.01)
*A61K 9/08* (2006.01)
*A61K 9/107* (2006.01)
*A61K 9/19* (2006.01)
*A61K 9/20* (2006.01)
*A61K 9/48* (2006.01)
*A61K 36/73* (2006.01)
*A61K 36/9066* (2006.01)
*A61K 38/01* (2006.01)
*A61K 38/39* (2006.01)
*A61K 47/10* (2017.01)
*A61K 47/14* (2017.01)
*A61K 47/26* (2006.01)
*A61K 47/36* (2006.01)

(52) U.S. Cl.
CPC .............. *A61K 31/12* (2013.01); *A61K 9/08* (2013.01); *A61K 9/1075* (2013.01); *A61K 9/19* (2013.01); *A61K 9/20* (2013.01); *A61K 9/48* (2013.01); *A61K 36/73* (2013.01); *A61K 36/9066* (2013.01); *A61K 38/014* (2013.01); *A61K 38/39* (2013.01); *A61K 47/10* (2013.01); *A61K 47/14* (2013.01); *A61K 47/26* (2013.01); *A61K 47/36* (2013.01)

(58) Field of Classification Search
CPC ..................................................... A61K 31/12
See application file for complete search history.

(56) References Cited

U.S. PATENT DOCUMENTS

2010/0179103 A1 7/2010 Desai

FOREIGN PATENT DOCUMENTS

| WO | WO 2010/010431 A1 | 1/2010 | |
| WO | WO-2010013224 A2 * | 2/2010 | ............. A61K 31/12 |
| WO | WO-2015025263 A1 * | 2/2015 | ............. A23L 27/10 |

OTHER PUBLICATIONS

Gomez-Estaca et al., Improving antioxidant and antimicrobial properties of curcumin by means of encapsulation in gelatin through electrohydrodynamic atomization, Food Hydrocolloids, 2017, vol. 70: 313-320.*
Comblain et al., Curcuminoids Extract, Hydrolyzed Collagen and Green Tea Extract Synergically Inhibit Inflammatory and Catabolic Mediator's Synthesis by Normal Bovine and Osteoarthritic Human Chondrocytes in Monolayer, PLoS ONE 10.3 (2015): e0121654.*
Gómez-Estaca J., et al., "Improving antioxidant and antimicrobial properties of curcumin by means of encapsulation in gelatin through electrohydrodynamic atomization," *Food Hydrocolloids*, 70:313-320 (2017).
Jiang, Y. et al., "Self-emulsifying drug delivery system improves preventive effect of curcuminoids on chronic heart failure in rats," *Saudi Pharmaceutical Journal*, 26:528-534 (2018).
Comblain, F. et al., "Curcuminoids Extract, Hydrolyzed Collagen and Green Tea Extract Synergically Inhibit Inflammatory and Catabolic Mediator's Synthesis by Normal Bovine and Osteoarthritic Human Chondrocytes in Monolayer," *PLoS ONE*, 10(3):e0121654, 20 pages (2015).
Emea, "ICH Topic Q 1 A (R2) Stability Testing of new Drug Substances and Products," *European Medicines Agency*, 20 pages (2003).
Louis, M.J., et al., "Two-Stage Supramolecular Self-Assembly-Directed Collagen-Peptide-Decorated Liposomal Complexes of Curcumin Microspheres with Enhanced Solubility and Bioavailability," *ACS Omega, American Chemical Society*, (2023) 10 pages.

* cited by examiner

*Primary Examiner* — Svetlana M Ivanova
(74) *Attorney, Agent, or Firm* — Crowell & Moring LLP

(57) ABSTRACT

Formulations comprising complexes of peptides with hydrophobic bioactive molecules are described herein. The invention more specifically relates to collagen peptide and curcuminoid complexes and compositions comprising the complexes. The compositions and formulations comprising the protein hydrolysate peptide-hydrophobic bioactive molecule complexes are water-soluble, stable at physiological and acidic pH, synergistically enhance the systemic bioavailability of the biomolecules and peptides, and are capable of delivering a high therapeutically effective amount of the bioactive molecules via oral route. The compositions and formulations comprising the collagen peptide-curcuminoid complexes provide significantly high levels of bioavailable curcuminoids that are water soluble and stable at physiological and acidic pH along with significant anti-inflammatory effects offered by collagen peptides. The invention further provides a process for preparing the peptide-bioactive molecule complexes, compositions and oral formulations comprising the collagen peptide-curcuminoid complex.

12 Claims, 17 Drawing Sheets

Control

C95

CCL

COMPLEXES COMPRISING COLLAGEN PEPTIDES AND CURCUMINOIDS AND COMPOSITIONS THEREOF

REFERENCE TO EARLIER FILED APPLICATION

This application in a continuation application of U.S. application Ser. No. 16/773,494, filed Jan. 27, 2020, which claims the benefit of the filing date of Indian Provisional Patent Application No. IN201941003319, filed Jan. 28, 2019, disclosures of which are incorporated, in its their entirety, by this reference.

TECHNICAL FIELD

The present invention relates to complexes comprising small hydrophobic bioactive molecules and protein hydrolysate peptides, and water-soluble formulations comprising them. More specifically, the invention relates to complexes comprising collagen peptides and curcuminoids and formulations comprising the complexes. The formulation described herein comprising the collagen peptide-curcuminoid complexes are water-soluble, stable at physiological and acidic pH, and enhances the systemic bioavailability of curcuminoids with enhanced elimination half-life, thus delivering therapeutically effective amount of curcuminoids via oral route. The invention thus provides a novel route for the simultaneous oral delivery of therapeutically relevant dosage of both collagen peptides and curcuminoids. The invention further provides the process for preparing the collagen peptide-curcuminoid complex.

BACKGROUND

Oral delivery of bioactive molecules is the preferred route of administration by consumers and manufacturers for their ease and convenience contributing to higher adherence, lower production costs and greatest versatility with respect to optimization of drug delivery over other forms. However, oral delivery has been limited to a few molecules as various difficulties with respect to the physical and chemical properties of bioactive molecules and the physiology of the gastrointestinal (GI) tract. The main consequence of the poor absorbance and degradation of bioactive molecules administered orally is low bioavailability. Increasing dose to overcome the poor bioavailability problem increases concerns about both potential adverse effects, formulation difficulties and excessive costs. Another challenge to develop formulations of biologically active molecules is their stability in formulations. Effective solutions for overcoming issues of bioactive molecules such as hydrophobicity, instability, rapid biotransformation to inactive metabolites have yet to be identified, so that therapeutically effective concentrations can be delivered without increasing dosages. In the case of nutraceuticals and functional food, food-grade delivery forms or delivery technologies employing food components or molecules from food is a great challenge.

Proteins are essential components of life and are widely distributed in plants and animals. They have important physiological role. Isolated proteins have been characterised to be macromolecules composed of amino acids. Once consumed, they are getting hydrolysed to peptides and amino acids having definite nutritional properties. Several food protein hydrolysates composed of peptides and amino acids are available as food ingredients. Collagen peptides are one such group of collagen protein hydrolysates that are shown to be having functional benefits for skin, bone, joints, and gastrointestinal tract. Collagen peptides are reported to improve the skin health (reduces wrinkles, increases hydration, increases the skin radiance), bone health (bone density and cartilage formation), joint health (reduces osteoarthritis pain and increases joint flexibility) and gastro protective. However, its anti-inflammatory effect has been shown to be low and very often require high dosage (3 to 10 g/day) and longer duration of supplementation (6 months to one year). So there exist a practice of co-administration of anti-inflammatory phytonutrients like curcuminoids, *Boswellia* extract, ginger extract etc. along with collagen peptides with a view to modulate the efficacy.

Considering the requirement of relatively high dosage of protein hydrolysates, the very often used delivery format is food, especially in the form of sachets (ready-to-drink powder). Since the bioactive molecules are hydrophobic, water insoluble and having strong colour and taste, their incorporation into peptides is very difficult. One of the practices is to make physical mixtures using a large excess of synthetic emulsifier like polysorbate for supplementation. Such formulations suffer from serious draw backs of poor bioavailability of the phytonutrients, undesirable colour and taste, staining tong, hygroscopicity, and requirement of special packaging.

Curcuminoids are natural polyphenolic compounds derived from turmeric (*Curcuma longa* L). The mixture of curcumin, demethoxycurcumin (DMC) and bisdemthoxycurcumin (BDMC) isolated from turmeric rhizomes are known as 'curcuminoids', and are often referred to as 'curcumin'. Curcuminoids have been shown to be modulators of multiple intercellular signalling pathways linked to inflammation, to proliferation, growth, invasion, drug sensitivity, angiogenesis and cancer cell metastasis in many cell based assays.

Although curcuminoids has shown significant efficacy in cell culture studies, it has shown limited efficacy in clinical studies when administered in conventional oral formulations, with low nanomolar levels of the parent compound and its glucuronide and sulphate conjugates found in the peripheral or portal circulation. It has been reported that serum levels in humans after an oral dose of 3 g curcumin alone were either undetectable or very low. Thus, the serum curcuminoids level is insufficient to provoke the desired beneficial effect of this compound, and cannot be achieved by the mere consumption of turmeric or curcuminoids.

Curcumin is highly hydrophobic and usually is not present in dissolved form when delivered as a component of commonly available nutraceuticals. Effective concentration for curcumin to exert any of the cellular effects has been demonstrated to be in the range of at least 100-2,000 nanomolar (0.1-2 micromolar) levels in vitro, but currently available curcumin supplements lead to negligible, low nanomolar blood levels. The poor oral bioavailability may result from its poor solubility, gastrointestinal instability, poor pharmacokinetic profile, or a combination of these factors. In particular, characteristics of curcumin such as chemical instability at neutral and slightly alkaline pH, its hydrophobic nature, and typically its insolubility at acidic pH when delivered as a dry powder in existing supplements. Most of the curcumin is never absorbed and is excreted. The susceptibility to autoxidation, its rapid biotransformation to conjugated glucuronides/sulfates (conjugative metabolism) by reaction of curcumin's phenolic hydroxyl groups and high "first pass" clearance leads to its poor permeation from the intestinal lumen to the portal blood.

These disadvantages have posed a major impediment in the development of various therapeutic and prophylactic applications of curcuminoids in spite of its pleiotropic pharmacological properties. To improve the bioavailability, sophisticated drug delivery systems are still being researched.

WO2015025263A1 describes a curcumin composition for increasing the bioavailability of curcumin mainly due to the presence of volatile oil of turmeric. The curcumin mixture comprises curcumin dry crystals, volatile oil, fixed oil whereas water extract comprises soluble proteins, dietary fibers and carbohydrates extracted from turmeric, along with a natural emulsifier isolated from *Quillaja saponaria* and lecithin. The curcumin composition showed bioequivalence with 500 mg curcumin capsules.

U.S.20100179103 A1 describes a method of increasing the delivery of curcumin by complexing it with cyclodextrins. The combination of cyclodextrins and curcumin in pre-clinical inflammation models demonstrated efficacy superior to both the positive control and curcumin. The curcumin are delivered by cyclodextrins which are cyclic oligomers of glucose, by forming inclusion complexes with the insoluble curcumin molecule which fit into the lipophile-seeking cavities of the cyclodextrin molecule.

WO2010/010431 describes a liquid and semisolid self-emulsifying curcumin formulations based on a lipid carrier system of PEG fatty acid esters which showed improved bioavailability compared to an aqueous suspension of curcumin after oral administration to rats.

WO 2010/013224 describe curcumin nanoparticles and curcumin bound to chitosan nanoparticles to provide improved oral bioavailability of curcumin in mice compared to curcumin orally administered in olive oil.

Researchers Gomez-Estaca et al., (Food Hydrocolloids, 2017, Volume 70: 313-320) have attempted encapsulation of curcumin in gelatin through electrohydrodynamic atomization. Water solubility of curcumin was found to increase by 38.6 folds. The antioxidant and antimicrobial properties of the encapsulated curcumin was also found to be improved. However, there is an absence of any information on the bioavailability of curcuminoids, the efficacy of curcumin-gelatin formulation on anti-inflammatory effect or any other pharmacological effect or any dosage information for the oral delivery of therapeutically relevant doses of curcuminoids and gelatin. Moreover, gelatin is a very high molecular weight protein, which forms gels and thick solutions in water which provides challenges to preparation of oral formulations.

Lately, self-emulsifying drug delivery system (SEDDS) have been shown to improve the solubility and bioavailability of curcuminoids. The ameliorative effect of curcuminoid SEDDS are reported to be markedly better than that of suspension of curcuminoids in rat models for chronic heart failure (Jiang, Yunbin et al., *Saudi Pharmaceutical Journal*: SPJ 26.4 (2018): 528-534. PMC. Web. 5 Jul. 2018). However, SEDDS faces disadvantages due to presence of high amount of surfactant, contradiction in correlation of in vitro model to in vivo studies, lack of human volunteer study and effect of conversion of SEDDS to final administrable dosage form on pharmacokinetic behaviour of the drug.

Researchers Comblain, Fanny et al. (Ed. Christos Chadjichristos. *PLoS ONE* 10.3 (2015): e0121654. PMC. Web. 6 Jul. 2018) studied the in vitro effects of curcuminoid extract, hydrolyzed collagen and green tea extract alone and in combination on monolayer cultured normal bovine and human osteoarthritic chondrocytes. The in vitro effects for the combination of the nutraceuticals were significantly effective over the ingredients alone in providing beneficial effects on chondrocytes culture in inflammatory conditions. However, the data on combination studies show only a physical mixture of the antioxidant green tea extract with collagen peptides. There is no disclosure on any possible molecular interactions of green tea extract and collagen peptides or on its solubility, bioavailability, or any synergic effects.

Solid dosage forms for oral delivery of curcuminoids in prior art have attempted reduction in particle size of curcumin to form suspensions; modification of crystalline form; entrapment of curcumin molecules in liposomes or oil/lipid particles; use of polymer carriers embedded with curcumin to form dispersions or polymer loaded nanoparticles; and, formation of inclusion compounds with cyclodextrins/phosphatidylcholines, to increase solubility, stability and accessibility in or to the gastro-intestinal tract. However, most of them are not water soluble, and only dispersible. Their stability in water and under pH conditions of GI tract is also very poor.

Curcuminoid formulations using various macromolecular carrier forms such as dietary fiber, proteins, cyclodextrin, and phospholipids etc. are unsuccessful to enhance the bioavailability. These methods failed to provide completely water soluble curcuminoids in stable formulations in the pH range from 2 to 7. They also failed in the delivery of bioactive free curcuminoids over conjugated curcuminoids such as curcumin glucuronides or sulfates. Their half-life in blood was very low indicating the inability to stay for longer duration at significantly high concentrations.

Proteins like albumin have been used in the formulation of curcuminoids. For protein-based formulations, the bioactive hydrophobic molecules are first of all dissolved in organic solvents like DMSO, chloroform, methylene dichloride, acetone etc. and then added to protein solution for inclusion in their hydrophobic pockets of 3 dimensional structure. The loading levels of molecules like curcuminoids is also very low and may provide nano particles of less than 100 nm size in a very low yield. The preparation includes use of toxic organic solvents, the very low levels of curcumin loading, low yield, nano form and high cost very often remains as a challenge for its usage in food and nutrition field. These becomes critical where phytonutrients are used as food supplements, like Sachet or beverages.

Therefore, there exists an acute need for stable, water-soluble, highly effective, food-grade biologic compositions and formulations which can provide better bioavailability and hence more efficacious oral delivery in various food and pharmaceutical delivery forms. The importance of such compositions and formulations increase when they become food-grade safe, by avoiding the use of toxic organic solvents, are stable, water soluble and suitable for oral consumption as and in food and beverages. The water based, water soluble, non-NANO (<100 nm) and stable food-grade formulations with 10 to 20% (w/w) of bioactive molecules employing functional materials such as protein hydrolysates which itself has its own therapeutic activity when consumed at physiologically relevant dosage.

The present invention overcome these difficulties by providing a peptide-bioactive molecule complex in an encapsulated and stable form of peptide networks. Collagen peptides and curcuminoids are primarily used to explain the present invention.

SUMMARY

A water-soluble formulation comprising peptides from protein hydrolysates, and hydrophobic bioactive molecules, and method of making this formulation are described herein.

One embodiment of the current invention is a water soluble pharmaceutical composition comprising: (a) an effective amount of one or more hydrophobic bioactive molecules; (b) water-soluble peptides derived from protein hydrolysates; and (c) an emulsifying agent, wherein the water soluble protein hydrolysate peptides form an amorphous and nano-sized (100-1000 nm) non-covalent complex with the hydrophobic bioactive molecules.

In one embodiment, the hydrophobic bioactive molecules for the water soluble formulation described herein are selected from the group consisting of curcuminoids, flavonoids, stilbenes, carotenoids, saponins, terpenes, terpenoids, and chlorophyll. In one embodiment, the hydrophobic bioactive molecules are present at a concentration in the range of 1 to 25% in the formulation disclosed herein.

In one embodiment, the protein hydrolysate peptides are present at a concentration in the range of 10 to 90% in the composition.

In another embodiment, the composition provides oral administration of both the protein hydrolysate peptides and the bioactive molecules together in their physiologically relevant dosage without solubility or stability issues.

In one embodiment, the co-administration of hydrophobic bioactive molecules in the peptide matrix may help synergistic pharmacological effects and better bioavailability of the bioactive molecule.

In one embodiment, the composition described herein is stable at physiological pH.

In one embodiment, the composition described herein is stable at acidic pH.

In one embodiment, the hydrophobic bioactive molecules are curcuminoids. In one embodiment, the protein hydrolysate peptides are 1000-5000 Da in size.

In one embodiment, the protein hydrolysate peptides are collagen peptides. In one embodiment, the curcuminoids are complexed with and encapsulated in the collagen peptide matrix.

In one embodiment, the bioactive molecules comprising the formulation exhibit enhanced solubility and stability as compared to unformulated bioactive molecules. In one embodiment, the pharmaceutical composition disclosed herein exhibits increased bioavailability, increased absorption and longer half-life of the bioactive molecules after oral administration to a subject, as compared to unformulated bioactive molecules.

In one embodiment, the bioactive molecules comprising the complexes disclosed herein exhibit increased cellular permeability, as compared to unformulated bioactive molecules.

In one embodiment, the formulation disclosed herein exhibits increased anti-inflammatory effects as compared to unformulated bioactive molecules.

In one embodiment, the formulation disclosed herein is orally administered either as capsules, tablets, softgels, beadlets, liquid solution, liquid suspension, and liquid emulsion or as powder sachets (drinks) format for enhanced bioavailability of the bioactive molecules.

In one embodiment, it is administered orally at a dose of 100 to 500 mg/dose in the form of tablets, capsules or softgel to deliver 25 to 100 mg of bioactive molecule in a bioavailable format.

In one embodiment, it is administered orally at a dose of 1000 mg to 5000 mg per sachet, once or twice per day, to deliver minimum 100 to 500 mg of bioactive molecules per day along with 1 to 10 g of peptides/dosage/day.

In one embodiment, the powder form of the formulation disclosed herein is amorphous.

One embodiment of the current invention is a method of making a water-soluble pharmaceutical composition comprising collagen peptides and curcumin, wherein the collagen peptides form a water soluble, stable, amorphous and nano-sized non-covalent complex with the curcuminoids., the method comprising the steps of: (a) micronisation of curcuminoids followed by emulsification by homogenisation with an emulsifier; (b) dissolving collagen peptides in water at a concentration range of 20 to 95%; (c) complex formation of curcuminoids with the collagen matrix by sonication with the emulsified curcuminoids from step (a) and the dissolved collagen peptides from step (b) and; (d) encapsulation of the complex from step (c) by making sub-micron sized micelle suspension by ultrasound mediated homogenisation; and (e) drying the submicron sized micelles from step (d) by spray drying or freeze drying or other low temperature drying techniques.

In one embodiment, the emulsifier is selected from the group consisting of lecithin, polysorbate, propylene glycol, sorbitol, glycerol, polyglycerol esters, *Quillaja* extract, and sugar esters.

Further scope of applicability of the present invention will become apparent from the detailed description given hereinafter. It should be understood that the description and the examples, while indicating embodiments of the invention, are given by way of illustration only, since various changes and modifications within the spirit and scope of the invention will become apparent to those skilled in the art from the description. It is to be understood that the description and examples are explanatory and representative of the invention and in no way limit or restrict the invention as claimed.

DETAILED DESCRIPTION

Figure 1:
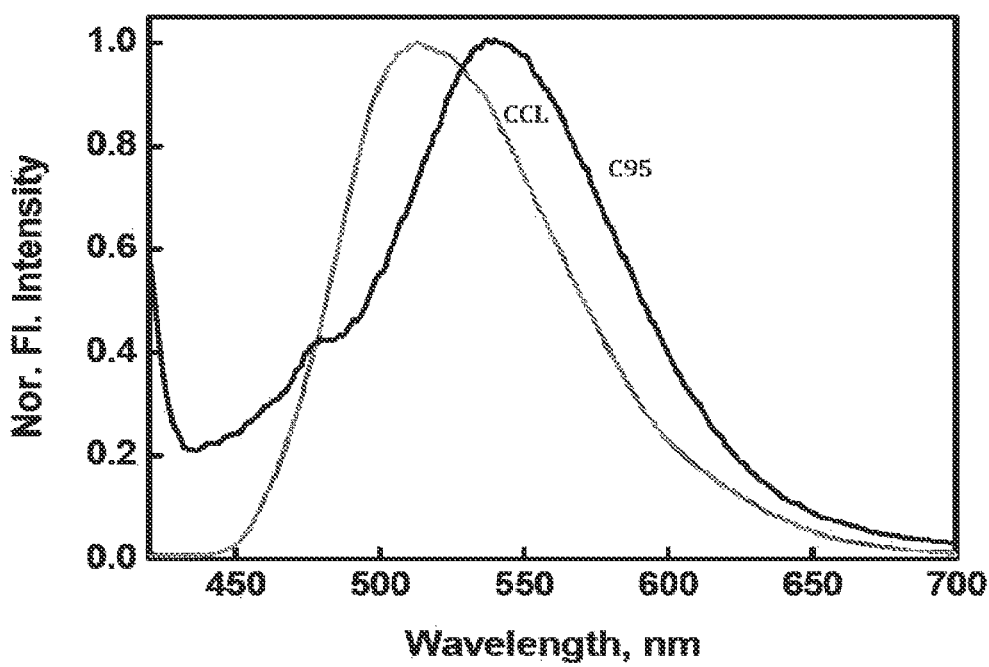
FIG. 1 shows fluorescence analysis of the CCL complex. C95—Curcuminoids with 95% purity isolated from turmeric rhizomes; CCL—Curcuminoids-collagen complex.

The invention is not limited to various embodiments given in this specification. The terms used in this specification generally have their ordinary meanings in the art, within the context of the invention, and in the specific context where each term is used. Unless otherwise defined, all technical and scientific terms used herein have the same meaning as commonly understood by one of skill in the art to which this invention pertains. Certain terms used herein are described below, or elsewhere in the specification to provide additional guidance to a practitioner regarding description of the invention. In case of conflict, the present document, including definitions will control.

As used herein, the terms 'comprising', 'including', 'having', 'containing', 'involving' and the like are to be understood to be open ended, i.e., to mean including but not limited to.

As used herein, the terms 'curcumin' and 'curcuminoids' are used interchangeably and indicate the biologic phenols obtained from the *Curcuma* plant. In the present application, 'curcuminoids' refers to the standard curcumin with not less than 95% purity isolated from turmeric rhizomes by solvent extraction with a composition of curcumin 72 to 80% w/w, DMC (demethoxycurcumin) 12 to 15% w/w and BDMC (bisdemethoxycurcumin) 3 to 5% w/w.

As used herein, the term "unformulated bioactive molecules" refers to hydrophobic biomolecules not in complex with any carrier molecules or matrix. It refers to bare bioactive molecules, without any extraneously added carrier molecules.

The term "unformulated curcuminoids" refers to curcuminoids not in complex with any carrier or delivery molecules or matrix. It includes the curcuminoids that are isolated from the turmeric rhizome and not bound to any other extraneously added carrier molecules.

As used herein, the term "effective concentration", "effective amount" means a concentration of the formulations described herein which can generate the desired effect in the subjects/patients, without leading to undesired levels of side effects. The effective concentrations of the formulations disclosed herein are given the various embodiments herein, as dosages of the formulation in different delivery formats.

As used herein the term "C95" refers to Curcuminoids with 95% purity isolated from turmeric rhizomes; "CP" refers to collagen peptide, "CCL" refers to curcuminoids-collagen complex.

The current invention provides water-soluble formulations comprising peptides from protein hydrolysates, and hydrophobic bioactive molecules, and method of making this formulation.

One embodiment of the current invention is a water soluble pharmaceutical composition comprising: (a) an effective amount of one or more hydrophobic bioactive molecules; (b) water-soluble peptides derived from protein hydrolysates; and (c) an emulsifying agent, wherein the water soluble protein hydrolysate peptides form an amorphous and nano-sized non-covalent complex with the hydrophobic bioactive molecules and acts as a matrix for its effective encapsulation in solution.

In one embodiment, the hydrophobic bioactive molecules for the water soluble formulation described herein are selected from the group consisting of curcuminoids, flavonoids, stilbenes, carotenoids, saponins, terpenes, terpenoids, and chlorophyll. In one embodiment, the hydrophobic bioactive molecules are present at a concentration in the range of 1 to 25% in the formulation disclosed herein.

In one embodiment, the protein hydrolysate peptides are present at a concentration in the range of 10 to 90% in the composition. In another embodiment, such peptides have nutritional properties and are derived from food proteins.

In one embodiment, the hydrophobic bioactive molecules are curcuminoids. In one embodiment, the protein hydrolysate peptides are 1000-5000 Da in size.

In one embodiment, the protein hydrolysate peptides are collagen peptides. In one embodiment, the curcuminoids are complexed with and encapsulated in the collagen peptide matrix, where peptides act as a protective coat of the water soluble bioactive micelle or liposomes or phytosomes formed between the emulsifiers and hydrophobic bioactive molecules.

In another embodiment, peptides provides a noodle like structure in which the micelles or liposomes or water miscible particles of the hydrophobic molecules are trapped and protected.

In one embodiment, it exhibits enhanced solubility and stability as compared to unformulated bioactive molecules. In another embodiment, the peptide network of the formulation swells in the gastrointestinal (GI) fluid and is acted upon by the GI enzymes to convert to smaller peptides and amino acids and the leached hydrophobic molecules get easily absorbed, thus enhancing bioavailability.

In one embodiment, the pharmaceutical composition disclosed herein exhibits increased bioavailability, increased absorption and longer half-life of the bioactive molecules after oral administration to a subject, as compared to unformulated bioactive molecules.

In one embodiment, the composition exhibits increased cellular permeability, as compared to unformulated bioactive molecules.

In one embodiment, the composition disclosed herein exhibits increased anti-inflammatory and antioxidant effects as compared to unformulated bioactive molecules.

In one embodiment, the composition disclosed herein is orally administered either as capsules, tablets, softgels, beadlets, liquid solution, liquid suspension, and liquid emulsion or as powder sachets (drinks) for enhanced bioavailability of the bioactive molecules.

In one embodiment, it is administered orally at a dose of 100 to 500 mg/dose in the form of tablets, capsules or softgel to deliver 25 to 100 mg of bioactive phytonutrient molecule in a bioavailable format.

In one embodiment, it is administered orally at a dose of 1000 mg to 5000 mg per sachet, once or twice a day, to deliver minimum 100 to 500 mg of bioactive molecules per day along with 1 to 10 g of peptides/dosage/day. In one embodiment, wherein the powder form of the formulation disclosed herein is amorphous.

In one embodiment, the method of making a water-soluble pharmaceutical composition comprising collagen peptides and curcumin, wherein the collagen peptides form a water soluble, stable, amorphous and nano-sized non-covalent complex with the curcuminoids, the method comprising the steps of: (a) micronisation of curcuminoids followed by emulsification by homogenisation with an emulsifier; (b) dissolving collagen peptides in water at a concentration range of 20 to 95%; (c) complex formation of curcuminoids with the collagen matrix by sonication with the emulsified curcuminoids from step (a) and the dissolved collagen peptides from step (b); (d) encapsulation of the complex from step (c) by making sub-micron sized micelle suspension by ultrasound mediated homogenisation; and (e) drying the submicron sized micelles from step (d) by spray drying or freeze drying.

In one embodiment, the emulsifier is selected from the group consisting of lecithin, polysorbate, propylene glycol, sorbitol, glycerol, polyglycerol esters, *Quillaja* extract, and sugar esters.

One embodiment of the pharmaceutical composition made by the method described above.

Collagen peptides support the integrity, elasticity, regeneration and strength of the connective tissues including skin, bones, cartilage, ligaments and tendons provide beneficial health effects to skin and bones, especially in improving joint mobility, ameliorating joint pain and the like associated with osteoarthritis.

In one embodiment, the present invention uses collagen hydrolysates or collagen peptides to prepare the complexes with hydrophobic bioactive molecules. In one embodiment, collagen peptides contains 19 amino acids. In one embodiment, the collagen hydrolysate or collagen peptides are prepared by enzymatic hydrolysis. In one embodiment, the collagen peptides used in the current invention are water soluble. Creating delivery forms with short peptides like collagen in solution is very difficult due to the fact that the short soluble peptides like collagen molecules does not have suitable conformation and 3dimensional structure with suitable hydrophobic pockets for engulfing hydrophobic molecules like curcuminoids.

In one embodiment, the short length water soluble collagen peptides used herein have molecular weight ranging from 2000 to 5000 Da. The water soluble peptides have a molecular weight ranging from 1000 to 20000 Da, more particularly 1000 to 5000 Da and more preferably 1000 to 3000 Da, obtained from the enzymatic hydrolysis of collagen, a high molecular weight animal protein of ~300 kDa.

In one embodiment, the short collagen peptides act as carrier or vehicle for hydrophobic and poorly bioavailable small bioactive molecules like curcuminoids to convert them into water soluble, easily dispersible curcuminoids with enhanced bioavailability when delivered orally. These properties are achieved by a complex formulation where by curcuminoids are associated with collagen peptides in a non-covalent, complex formation.

In one embodiment, these short collagen peptides successfully form complexes without the formation of any chemical cross links.

In one embodiment, the complexes disclosed herein possess interaction of curcuminoids with collagen peptides and also create strong Van der Waals force of attraction such as hydrogen bonding between collagen peptide molecules and curcuminoids.

In one embodiment, the strong interaction between emulsified curcuminoids and short collagen peptides results in a protective coating of the curcuminoids micelles or liposomes or phytosomes with collagen peptides to attain better stability in vivo. The interaction also results in an increase in the water solubility of hydrophobic curcuminoids, increased bioavailability of curcuminoids, and hence improved therapeutic efficacy.

In one embodiment, the present invention of collagen peptide-curcumin complex claim superiority a mere physical mixture or water dispersible physical mixture formulated by mixing the collagen peptides and curcuminoids, in terms of its solubility, stability, bioavailability and bio-efficacy. The physical mixture results in a water-insoluble, indispersible (not-dispersible) mixture of curcumin that settles to the bottom within few seconds thereby making its consumption difficult. Such a mixture will have low bioavailability without any synergistic effect, and will lack in sensory appeal necessary for an edible product.

In one embodiment, compositions and formulations comprising the unique collagen peptide-curcuminoid complexes disclosed herein provide significantly high levels of bioavailable curcuminoids that is water soluble and stable at physiological and acidic pH along with significant anti-inflammatory effects offered by collagen peptides.

In one embodiment, the collagen peptide-curcuminoid complex is in a water soluble, stable, solid dosage form having a concentration of 100 to 250 mg curcuminoids in every 3 g of collagen peptides, preferably in 2 g collagen peptides, or more preferably in 1 g collagen peptides suitable for oral consumption which renders collagen peptides and curcuminoids bioavailable for enhanced efficacy on skin, bone, joint and gastrointestinal health.

In one embodiment, compositions and formulations comprising the collagen peptide-curcuminoid complexes can be conveniently made to deliver effective dose of curcuminoids orally. In one embodiment, the collagen peptide-curcuminoid complex in the composition disclosed herein leads to increase in the water solubility of curcuminoids and their in vivo stability.

In one embodiment, the collagen-curcumin compositions and formulations exhibit better absorption and bio-availability when consumed orally.

In one embodiment, the collagen peptide—curcuminoid complex disclosed herein can be formulated for oral consumption in solid and liquid dose forms such as pills, capsules, tablets, soft-gels, emulsions, solutions, syrups and the like for delivering effective dose of collagen peptides and curcuminoids orally.

In an embodiment, the collagen peptide—curcuminoid complex disclosed herein can be formulated into food and drink edible compositions like powder mixes, granules, ready-to-drink liquids, beverage powders, drink and dairy mixes, confectionaries, and dietary supplements to name a few, for delivering effective dose of collagen and curcuminoids orally.

In an embodiment, powder formulations of curcuminoid-collagen peptide complexes suitable for supplementation at 1 to 10 g/serving of collagen peptides and 250 to 500 mg curcuminoids/serving is achieved as single ready to drink water soluble powder. The formulation not only provides bioavailable forms of bioactive molecules like curcuminoids, but also provides therapeutically significant dosage of peptides like collagen peptides together for synergic effect.

In another embodiment, the oral formulation of curcuminoid collagen peptide complexes suitable for supplementation as a sachet/to consume along with water, milk or yogurt, soups, ice creams, etc.

Although the present invention has been illustrated and described herein with reference to the embodiments and examples disclosed herein, it will be readily apparent to those skilled in the art that other embodiments and examples may perform similar functions and/or achieve like results. All such equivalent embodiments and examples are within the spirit and scope of the present invention, are contemplated thereby, and are intended to be covered by claims put forth in the application.

EXAMPLES

The examples below illustrate the present invention and are non-limiting. The below exemplify representative embodiments of the invention, where all parts, proportions and percentages are by weight unless otherwise indicated. All fine chemicals, reagents, solvents and the like were commercially procured.

Collagen peptides from bovine, chicken and fish were purchased from Nitta Gelatin India Limited, Kochi, Kerala State, India. Phospholipids were purchased from Lipoid AG, Steinhausen, Switzerland. Curcumin 95% was taken from the quality assurance laboratory of Akay Flavours and Aromatics Pvt Ltd., Kochi, Kerala, India.

Example 1: Preparation of Curcumin-Collagen Complex: Preparation of Curcuminoid Suspension About 9.2 g of commercially procured curcumin with not less than 90% purity was mixed with 4.5 g of MCT oil and with 4.5 g of glycerine and heated for 30 min to get a uniform mass. 9 g of lecithin having a phosphatidyl choline content of 20 to 90%, most preferably 25 to 45%, was then dissolved in 50 mL of ethanol/water mixture by homogenization or sonication. The water dispersible curcumin mass was then added slowly to ethanol/water by sonication and further suspended in 200 mL water with high power ultrasound (1000 KW) as pulses of 1 to 3 seconds or homogenization. Ethanol was then evaporated under vacuum to obtain a water suspension of curcuminoids having an approximate particle size not more than 2 µm.
Preparation of Collagen Peptide-Curcuminoid Complex 70 g of commercially obtained collagen peptides was separately dissolved in 400 mL water by homogenization. The solution was slowly mixed with the curcuminoids suspension (275 mL) by high shear mixing, optionally heating. The solution was homogenized and then spray dried or freeze dried to obtain free-flowing, water-soluble, stable, collagen peptide-curcuminoids complex having total curcuminoids content of 10.2%.

Alternatively emulsifiers including lecithin, polysorbate, propylene glycol, sorbitol, glycerol, and polyglycerol esters, *Quillaja* extract, or sugar esters, can be used with and without lecithin to make collagen peptide-curcuminoids complexes.

Fatty oils including but not limited to sunflower oil, coconut oil, polyunsaturated fatty oils, olive oil or fish oil may be used instead of MCT oil.

The composition of ethanol/water can vary from 70:30 v/v to 95:5 v/v.

Temperature during formulation can vary from 50 to 80° C., depending on the stability of the bioactive substance.

Peptides can be derived from any food-grade proteins having water solubility and molecular weight ranging from 1000 to 10000, preferably 1000 to 5000, more preferably 1000 to 3000 Da.

The amount of curcumin can vary from 1 to 25% to produce curcumin-collagen complex with varying levels of curcuminoids content preferably less than 20%.

Example 2: Preparation of Curcumin-Fava Peptide Complex

Curcumin-fava peptide complex can be used by using the similar process disclosed in Example-1. The fava protein hydrolysate (i.e. fava peptide with molecular weight of around 3000 Da) and polysorbate 3 g was used instead of Glycerol.

Example 3: Preparation of Collagen Peptide-Gingerol Complex

Gingerol is the bioactive molecule from Ginger and is water insoluble. Supercritical ginger extract containing 40% of gingerols was used for the formulation. It is obtained as an oil soluble paste form (Oleoresin). No oils were used in this formulation as specified in example 1. Briefly, about 18 g of oleoresin was mixed with and 18 g of lecithin with heating in ethanol/water medium. The ethanol was then evaporated and emulsified in water containing 3% *Quillaja* extract. The water-soluble form is then mixed with the collagen peptide with molecular weight 5000 and again sonicated. The uniform solution is then kept for 2 h. The supernatant solution is separated and freeze dried to fine water-soluble powder. Gingerol content was 6.3%.

Example 4: Characterisation of Collagen Peptide-Curcuminoids Complex

Spectroscopic techniques such as Fluorescence, Ultraviolet, Infrared, and NMR were used to confirm the non-covalent complex formation of curcuminoids with peptides. The shifts in the characteristic peaks due to hydrogen bonding between the peptide bonds, amino acid side chains and curcuminoids were confirmed. Proton ($^1$H) and $^{13}$C NMR studies show the inclusion of curcuminoids in the collagen network. Powder X-ray diffraction studies and differential scanning calorimetric confirms the amorphous nature of the complex whilst electron microscopic studies provide information on particle size, surface morphology and molecular arrangements in the complex.

Solid-state Fourier-transformed infrared spectra (FTIR) was recorded on Shimadzu spectrophotometer 8700 using potassium bromide pellets, prepared by compressing the powder at 20 psi for 10 min on a KBr press (Shimadzu Analytical Pvt. Ltd., Mumbai, India). The spectra were scanned over the wave number range of 3600-400 cm$^{-1}$. Thermogram was recorded using a differential scanning calorimeter (DSC) (Mettler-Toledo India Pvt. Ltd., Mumbai, India), by heating the samples (3-5 mg) in the aluminum crimp pan at a rate of 10° C./min from 30 to 300° C. under nitrogen atmosphere. Powder X-ray diffraction studies (PXRD) were performed on a Bruker D8 Advance instrument: target Cu, k—1.54 A°, filter—Ni, voltage 40 kV, time constant 5 min/s; scanning rate 1° C./min (Bruker AXS GmbH, Karlsruhe, Germany). Scanning electron microscopic analysis (SEM) was done on SEM Jeol 6390 LA equipment (JEOL Ltd., Tokyo, Japan).

The enhanced bioavailability of curcuminoids presented in the form of collagen peptide-curcuminoid complexes was confirmed by measuring the plasma concentrations over 24 h time period as compared to unformulated curcuminoids with 95% purity (C95).

Example 4A: Fluorescence Analysis

The fluorescence analysis (FIG. 1) shows that, upon complexation CCL has an increased intensity of absorption. Curcumin exhibited an emission spectra max at 580 nm which on complex formation with collagen, decreased to 505 nm, indicating the inclusion of curcuminoids in a hydrophobic environment with hydrophobic interactions. Hence the blue shift in the complex indicates higher energy requirement for the excitation of molecule which further supports a stronger interaction (complexation) between the curcuminoids and peptides.

Example 4B: Ultraviolet/Visible Spectroscopy Analysis

Figure 2:
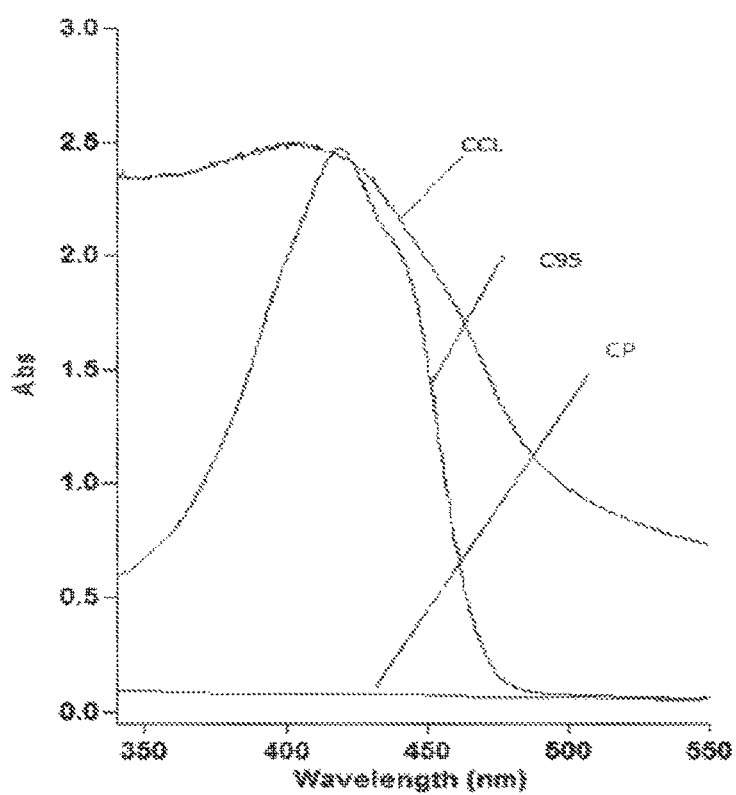
FIG. 2 shows Ultraviolet scan data of the CCL complex. C95—Curcuminoids with 95% purity isolated from turmeric rhizomes; CCL—Curcuminoids-collagen complex; CP—collagen peptide.

The Ultraviolet/Visible spectroscopy (FIG. 2) of C95, CP and CCL indicated an interaction between the curcumin moiety and the collagen in CCL. The absorption maxima of curcumin has shifted from 420 nm to 408 nm, a blue shift. The absorption peak of curcumin at 420 nm has also been altered to a hill like plot spread out from 190 to 500 nm in CCL. This is due to the influence of the peptide which along with the curcumin exhibits uniform UV absorption, a multipoint attraction where a wide range of chromospheres are available.

Example 4C: Fourier Transform Infrared Spectroscopy (FTIR)

Figure 3:
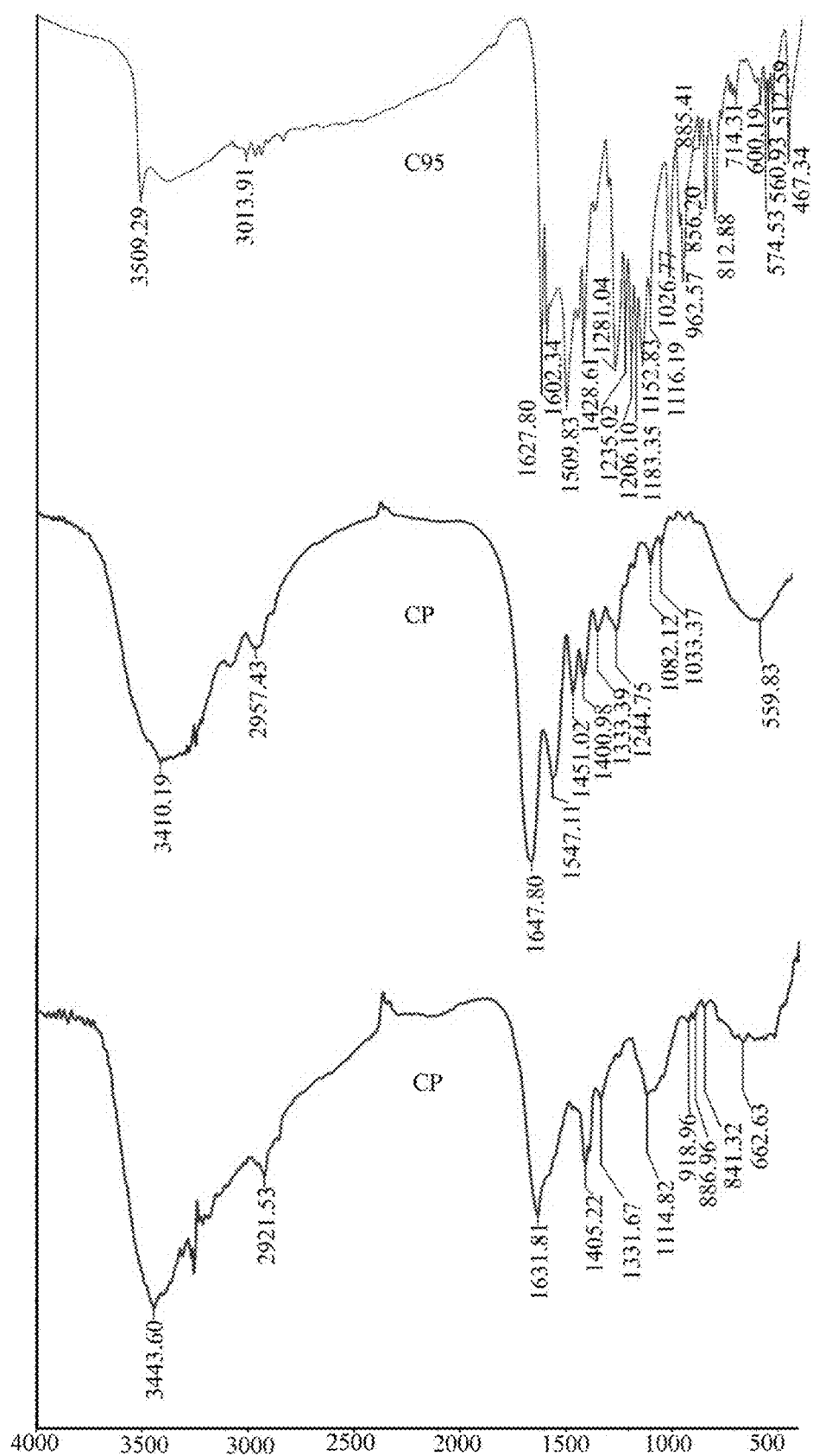
FIG. 3 shows FTIR data for the CCL complex. C95—Curcuminoids with 95% purity isolated from turmeric rhizomes; CCL—Curcuminoids-collagen complex; CP—collagen peptide.

Since, the complexation reaction was performed in water at almost neutral pH, the curcumin exists in an equilibrium between the keto and enol forms. In the keto form, the oxygen atom attached to the carbonyl group has a higher electronegativity due to the adjacent αβ unsaturation. This electronegativity of carbonyl oxygen attracts the lone pairs of the amide bond in the peptide chains, leading to intermolecular hydrogen bonding. This is evident from the shift of the 1647 cm$^{-1}$ of the amide bond to 1631 cm$^{-1}$ in CCL. The small peaks due to the stretching vibrations of enol-carbonyl groups at 1625 cm$^{-1}$ and 1599 cm$^{-1}$ were widened and observed as a shoulder of 1631 cm$^{-1}$ in CCL (FIG. 3). The peaks at 1426 cm$^{-1}$ in curcumin due to its C=C vibration is shifted to 1405 cm$^{-1}$ in CCL, indicating the presence of keto form and its hydrogen bonding. The absorption peak at 3510 cm$^{-1}$, which is the typical peak of the —OH group of the phenolic structure and the absorption peak at 3410 cm$^{-1}$ which is the typical peak of the normal amine group has fused together and got shifted to 3443 cm$^{-1}$ indicating an interaction between groups. Thus, the two —OH groups in the aromatic rings and the —OH and keto form of the keto-enolic form in curcumin has interactions with peptide bonds and terminal groups of peptides. Yet another possible reason for the shifts may be the hydrophobic interactions due to the inclusion of the curcuminoids in the hydrophobic pockets formed by the entanglement of random coiled peptides to form noodle-like structure for CCL.

Example 4D: NMR Studies

Figure 4A:
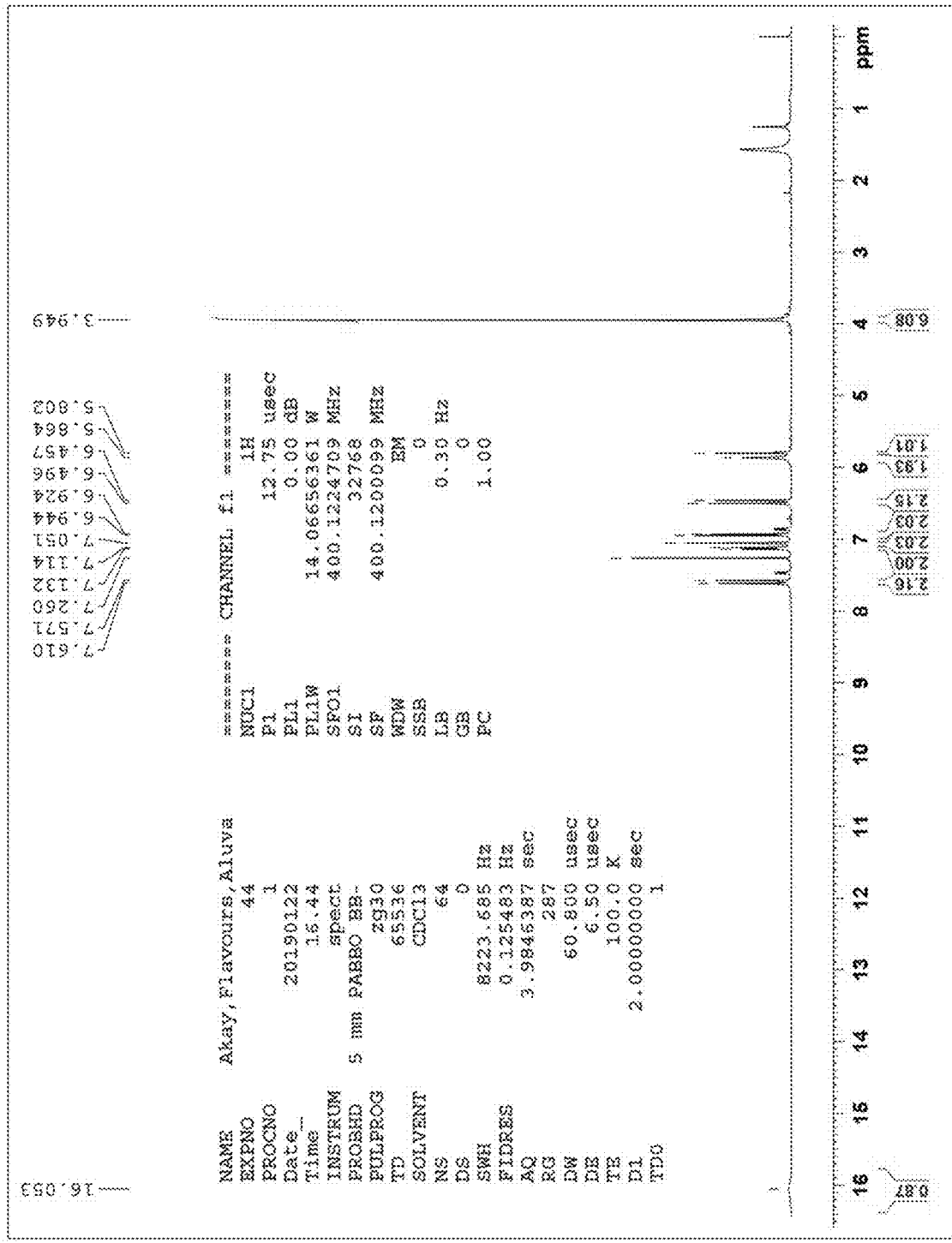
FIG. 4A shows $^1$H NMR data of C95—Curcuminoids with 95% purity isolated from turmeric rhizomes.
Figure 4B:
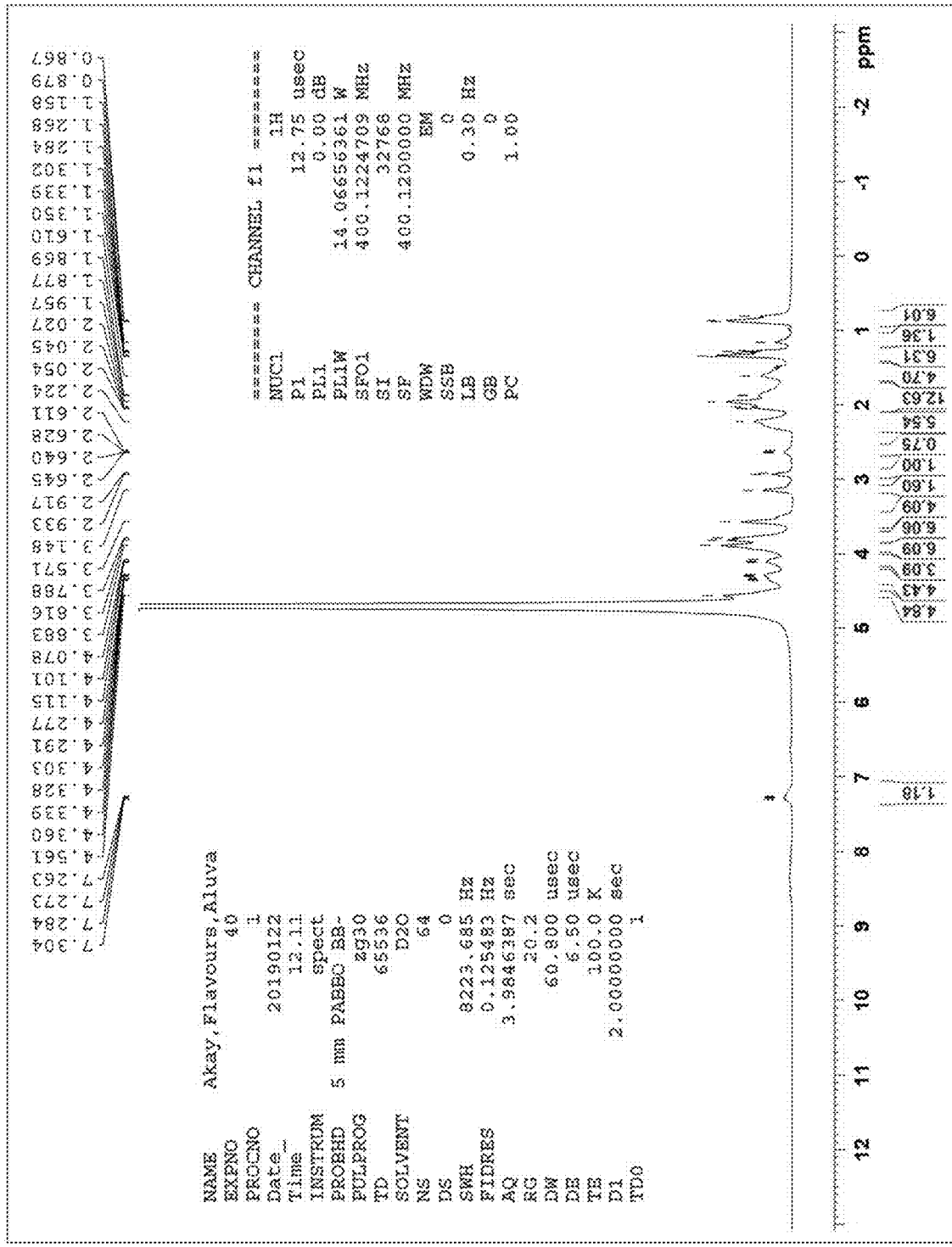
FIG. 4B shows $^1$H NMR data of CP—collagen peptide.
Figure 4C:
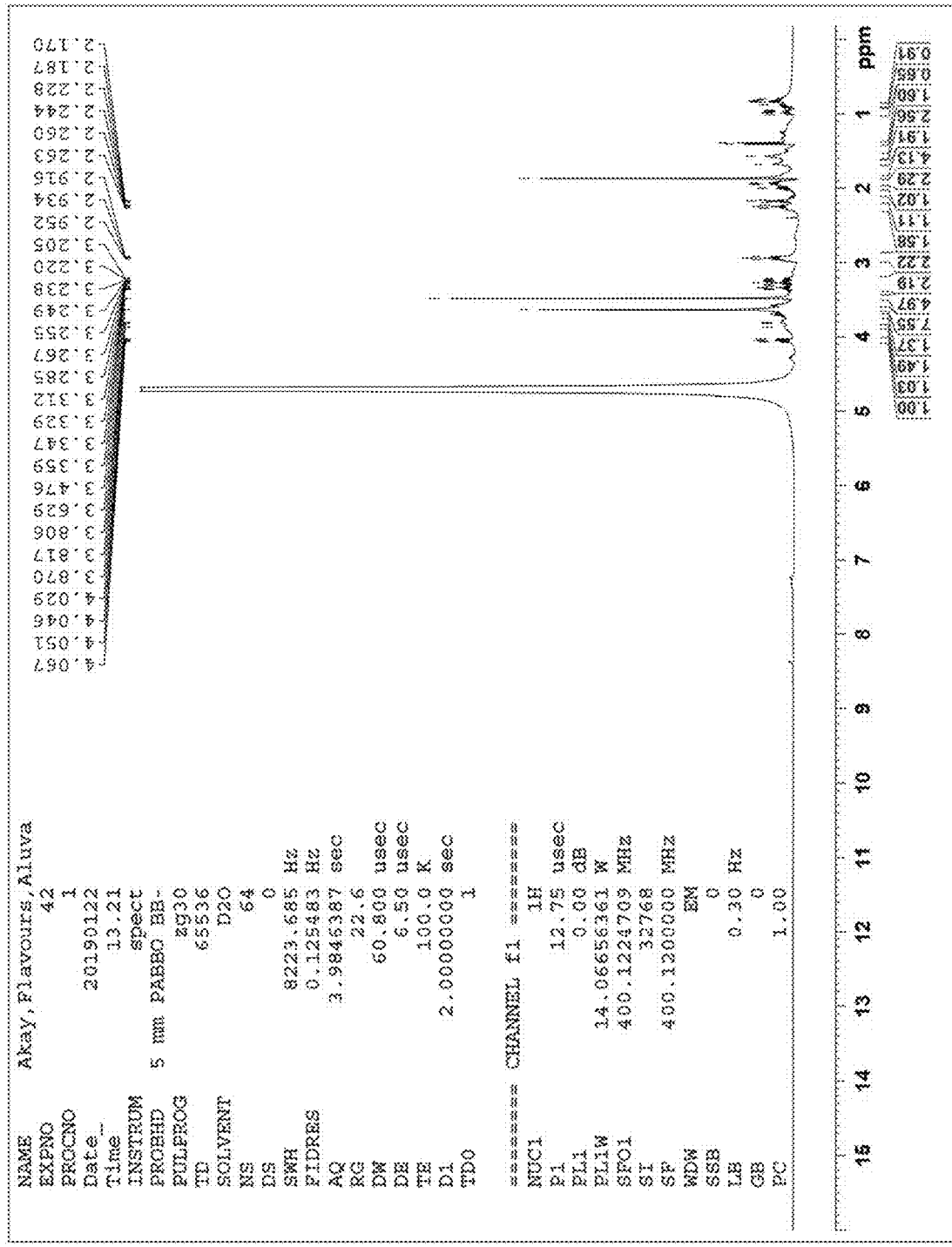
FIG. 4C shows $^1$H NMR data of CCL—Curcuminoids-collagen complex.

NMR studies revealed the extent of complexation in CCL. The $^1$H NMR data (FIG. 4A, B, C) of curcumin indicated the presence of a high shielded hydrogen atom (hydrogen of the enol form) with chemical shift at 16.053 ppm. Due to low shielding effect, the —OCH$_3$ group in the aromatic ring of curcumin exhibited sextet at 3.949 ppm. Upon compexation, the higher shielding effect of the enol form was lost. Similarly, the sextet at 3.949 ppm got shifted towards 3.629 ppm which indicated a further lowering of the shielding effect. This is due to the association of the peptide fractions at the —OH group adjacent to it. The hydrogen splitting raised from 6 to 7.55. 3.629 ppm which indicated a further lowering of the shielding effect. This is due to the association of the peptide fractions at the —OH group adjacent to it. The hydrogen splitting raised from 6 to 7.55.

Figure 5A:
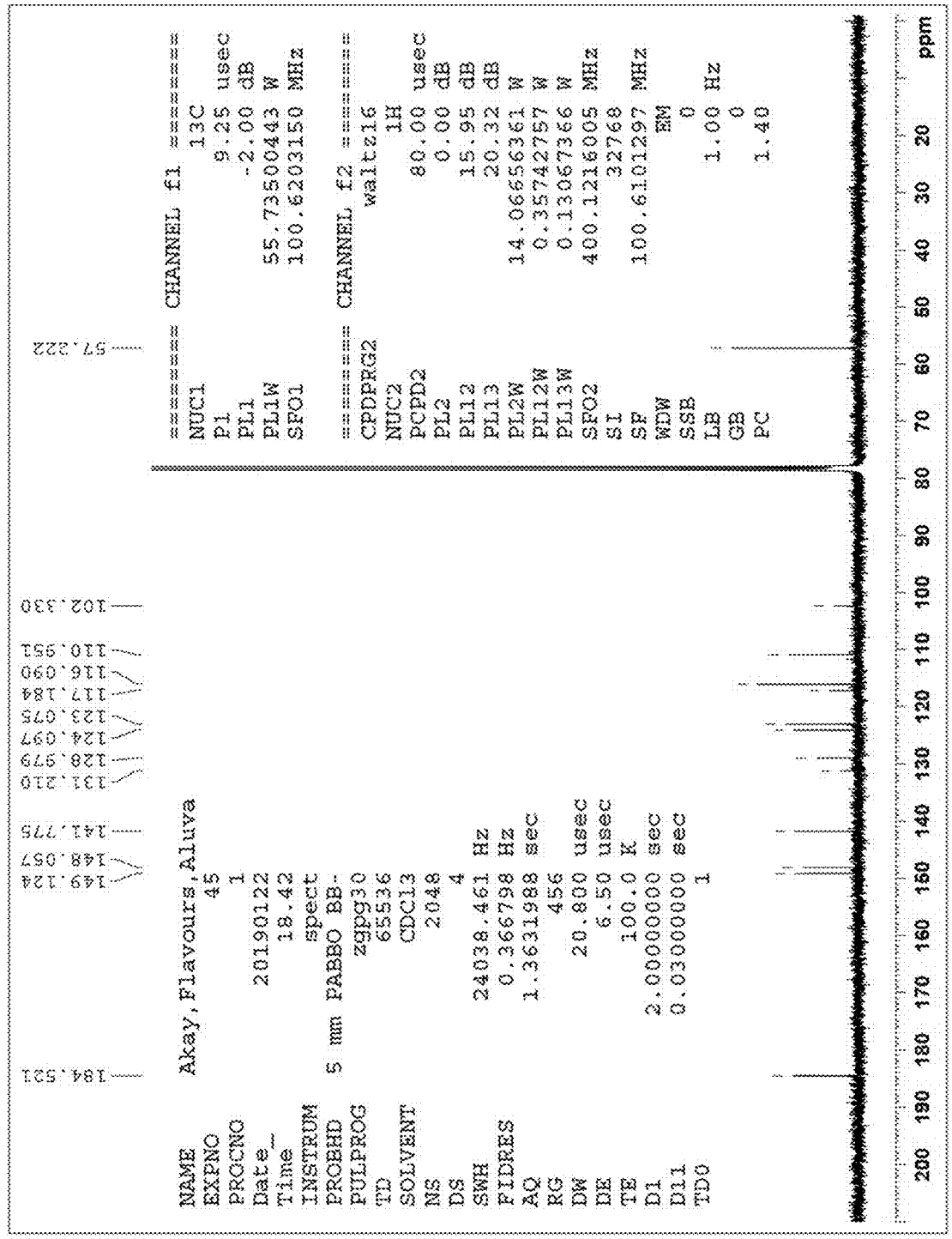
FIG. 5A shows $^{13}$C NMR data of C95—Curcuminoids with 95% purity isolated from turmeric rhizomes.
Figure 5B:
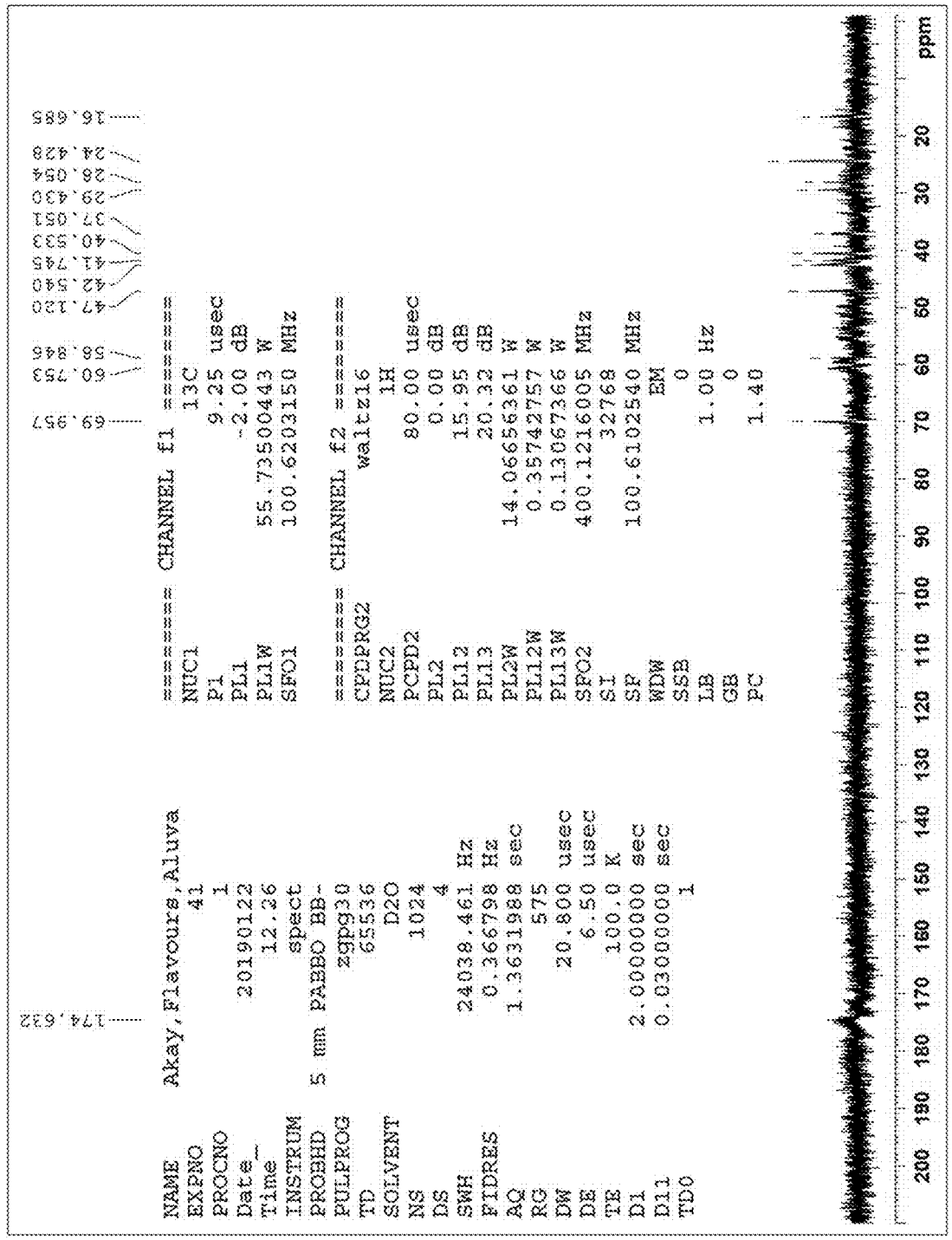
FIG. 5B shows $^{13}$C NMR data of CP—collagen peptide.
Figure 5C:
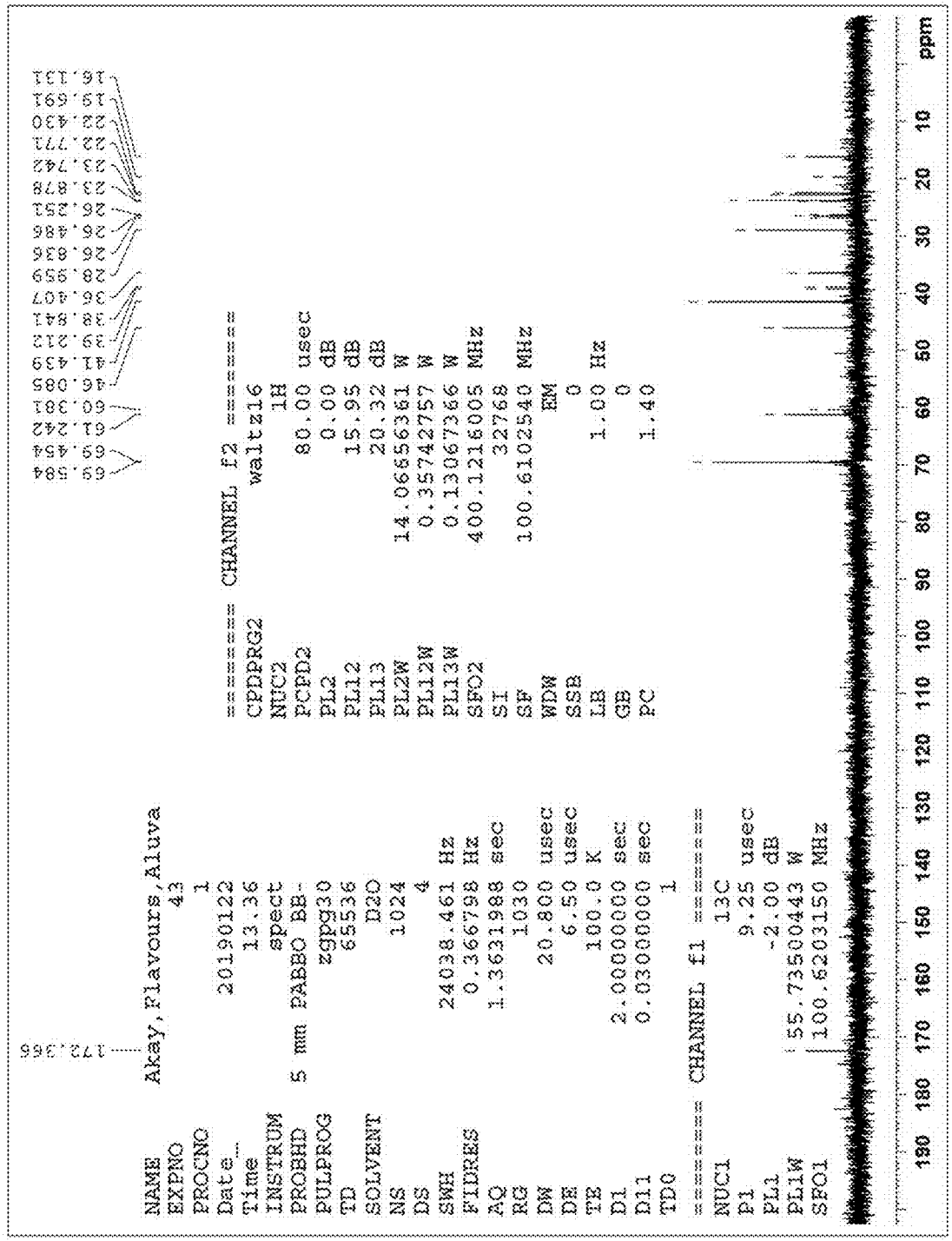
FIG. 5C shows $^{13}$C NMR data of CCL—Curcuminoids-collagen complex.

As per the $^{13}$C NMR data (FIG. 5A, B, C), the high shielded carbon of the keto-enolic form in curcumin was observed at 184.521 ppm. Upon CCL formation, the chemical shift lowered to 172.366 ppm. Similarly, the carbon atom of the —OCH$_3$ group, which was observed at 57.222 ppm in curcumin got further lowered to 46.085 ppm which indicated lowering of shielding effect. This too indicates the non-covalent force of attraction that may have formed in between the aromatic —OH group and the terminal —NH2 of the peptide.

Example 4E: Differential Scanning Calorimeter (DSC) Analysis

Figure 6:
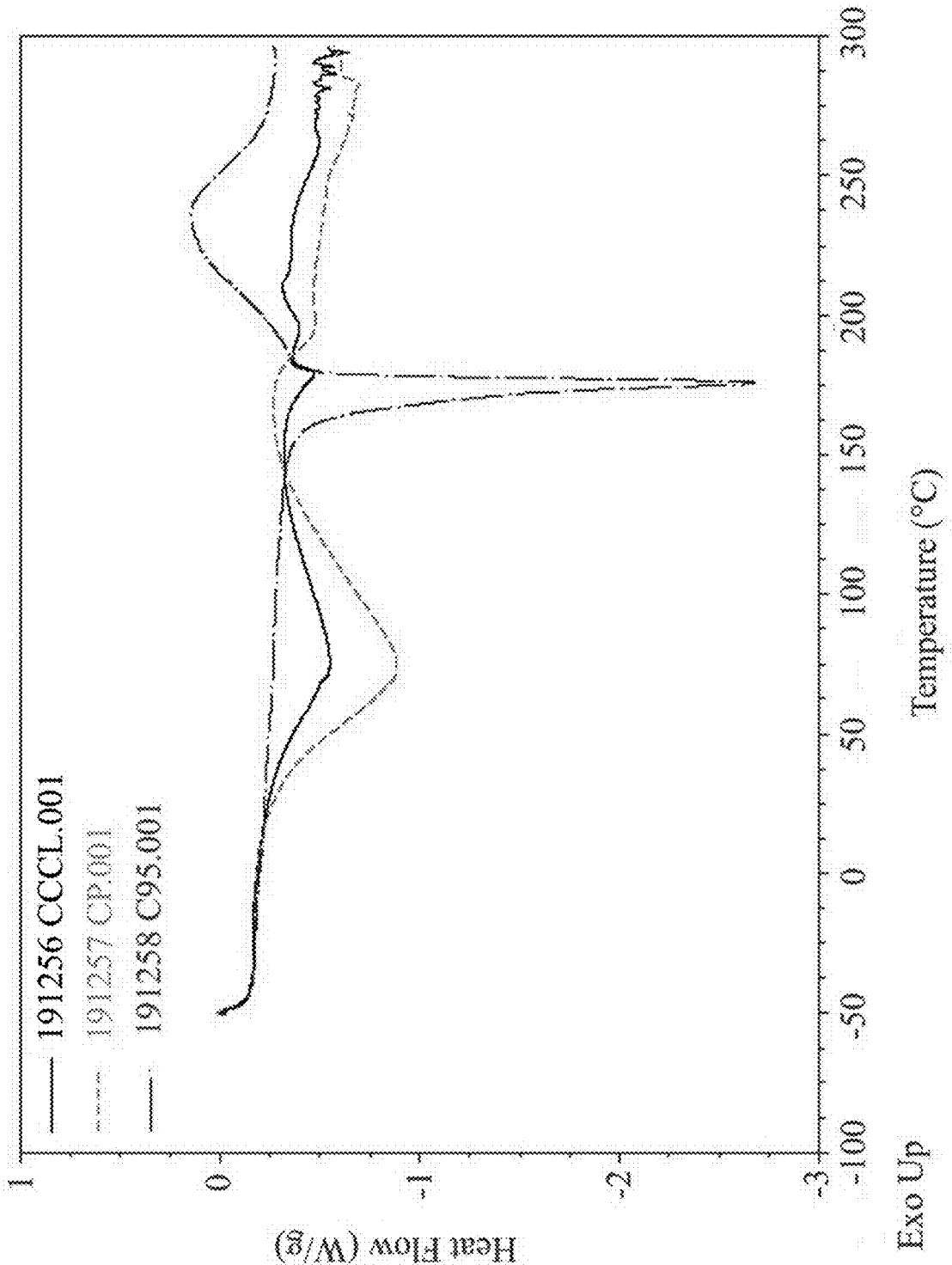
FIG. 6 shows DSC analysis of the CCL complex. C95—Curcuminoids with 95% purity isolated from turmeric rhizomes; CCL—Curcuminoids-collagen complex; CP—collagen peptide.

DSC analysis (FIG. 6) analysis exhibited a sharp endothermic shift at 175.74° C. for curcumin due to its melting. The collagen peptide exhibited a slight endothermic shift at 74.60° C. and 194.23° C. Upon complexation, the CCL exhibited a shift at 71.77° C., 179.49° C. and 196.33° C., indicating an adduct/bonding between the two entities. However, no sharp shift was observed, due to the amorphous nature of CCL.

Example 4F. Scanning Electron Microscopy (SEM)

Figure 7:
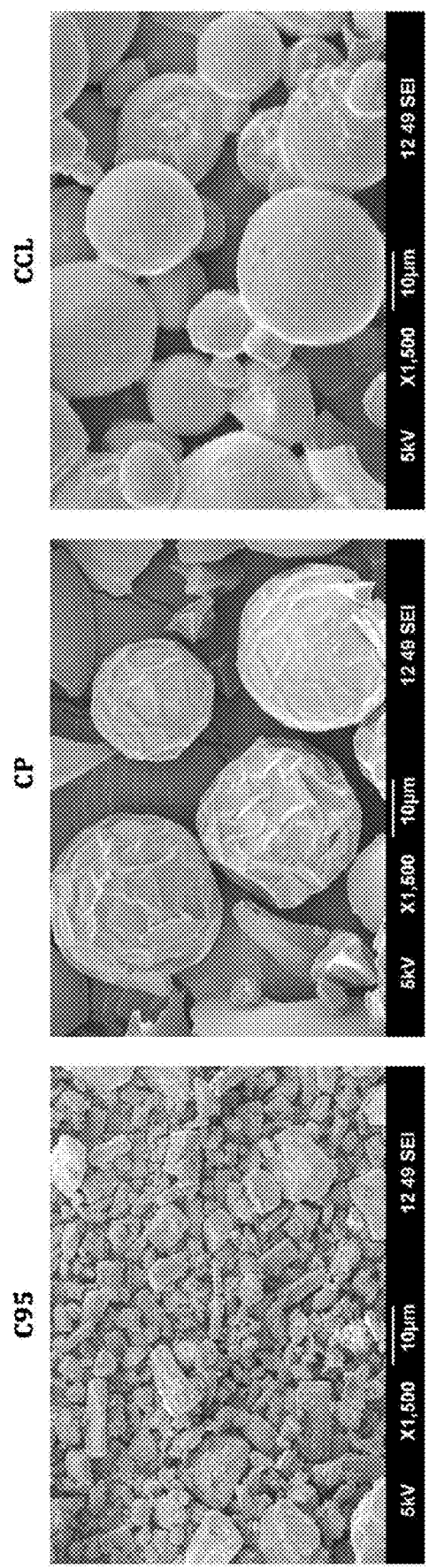
FIG. 7 shows SEM analysis of the CCL complex. C95—Curcuminoids with 95% purity isolated from turmeric rhizomes; CCL—Curcuminoids-collagen complex; CP—collagen peptide.

The scanning electron microscopy analysis of the powder samples (SEM) (FIG. 7) indicated the change in surface nature of the curcuminoids and collagen peptides. The curcuminoids were crystalline as evident from the needle shapes. Collagen peptide on the other hand is amorphous and forms spherical forms. The CCL complex is also spherical with smooth surface indicating the encapsulation of crystalline curcuminoids into the collagen network and its change into amorphous form.

Figure 8:
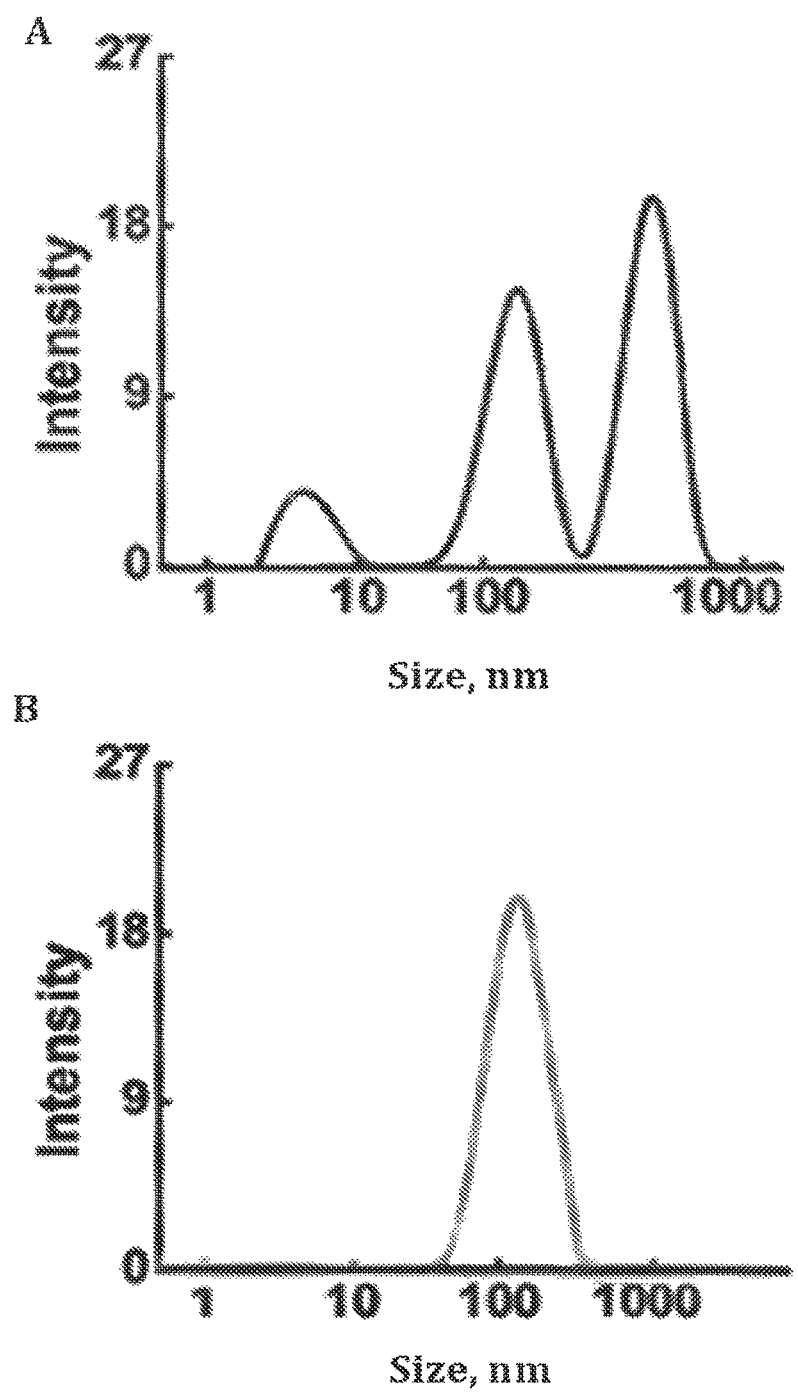
FIG. 8 shows particle size analysis of CCL solution (A), and particle size analysis of CCL solution filtered through a 420 nm filter (B).

Example 5: Particle Size and Transmission Electron Microscopy (TEM) Analysis of CCL in Water Example 5A: Particle Size Analysis Particle size/zeta potential of CCL in solution was analyzed by a dynamic light scattering Mastersize 3000 equipment of Melvern Pananalytical, USA. About 100 mg of curcuminoid-collagen complex was suspended in 10 mL distilled water for 1 h and shaken in a rotatory shaker. The supernatant solution was subjected to particle size analysis, which indicated two fractions having a mean particle size of less than 200 nm (150 to 200 nm) and relatively bigger particles of around 700 nm (600 to 700 nm). The solution was also filtered through a 420 nm Nylon filter and again subjected to particle size analysis. The particles were of around 176 nm (FIG. 8A, 8B).

Example 58: TEM Studies

Figure 9:
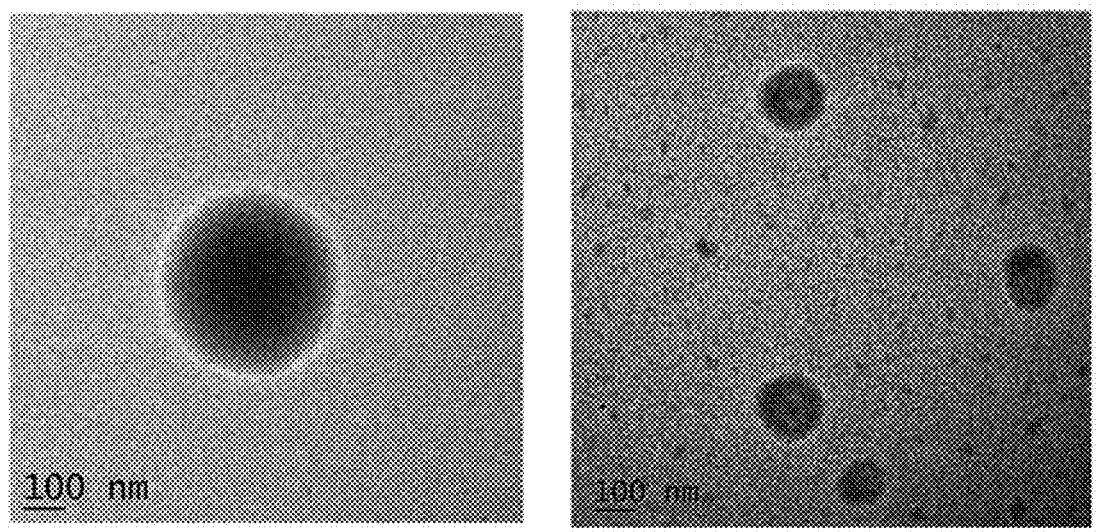
FIG. 9 shows TEM data. CP—Collagen peptide and CCL—Curcuminoid-collagen complex.

The morphology of particles in solution was visualized under transmission electron microscopy (JEM-2100, JEOL, Tokyo, Japan). Aqueous solution of curcuminoid-collagen complex was placed (20 μL) on a copper grid and allowed to dry at room temperature. After staining with 2% phosphotungstic acid, the thin film formed was subjected for TEM observation. TEM indicated the agglomeration of curcumin with collagen peptides, with strong association of both to observe as a single molecular solution (FIG. 9).

Figure 10:
FIG. 10 shows photographs of CCL and C95 water solutions. A. C95 in water, B. CCL in water and C. CCL in water after filtration through 200 nm filter.

Example 6: Water Solubility and Stability of Collagen Peptide-Curcuminoid Complex About 20 mg of curcumin 95% which contains 19 mg of pure curcumin by HPLC was weighed into a 100 mL standard flask and marked as C95. 100 mg of CCL which contains 19 mg of pure curcumin by HPLC was weighed into another 100 mL standard flask and marked as CCL. Both were made up to the volume using HPLC grade water and were sonicated in a bath sonicator for 5 min. It was centrifuged and the supernatant was subjected to HPLC analysis to measure the dissolved curcumin content. It is observed that curcuminoid content in C95 had 14 ng/mL and that in CCL was 2040 μg/mL, indicating enhancement in solubility of curcuminoids (FIG. 10).

Example 7: Storage Stability Of Collagen Peptide-Curcuminoid Complex

Storage stability studies were carried out as per the guidelines of International Conference on Harmonization (ICH) of technical requirements for registration of pharmaceuticals for human use (ICH, 2003). Briefly, the sample packets (10 g) of curcuminoid-collagen complex was sealed in a double layered polyethylene bags and were incubated at 40±2° C. and 70±5% relative humidity for a period of 6 months in a stability chamber (Remi, Mumbai, India). The samples were withdrawn at 0, 1, 2, 3, and 6 months and subjected to analysis for various physical and chemical parameters. Curcuminoids content, moisture content and microbial parameters comprising total plate count, yeast and mold, *Escherichia coli*, Salmonella and coliforms were measured, results are shown in Table 1.

TABLE 1

| Parameters | Specification | 0 month | 3 month | 6 month |
| --- | --- | --- | --- | --- |
| Appearance | Free flowing powder | Complies | Complies | Complies |
| Identification | HPLC | Complies | Complies | Complies |
| Colour | Yellowish orange | Complies | Complies | Complies |
| Curcumin content | >20% | 20.68% | 20.35% | 20.19% |
| Density | 0.4-0.8 g/mL | 0.42 g/mL | 0.42 g/mL | 0.42 g/mL |
| Microbiology | US-FDA (BAM) | | | |
| Total plate count | <3000 cfu/g | 100 cfu/g | 110 cfu/g | 100 cfu/g |
| Yeast & Mold | <100 cfu/g | <10 cfu/g | <10 cfu/g | <10 cfu/g |
| Coliforms | <3 MPN/g | <3 MPN/g | <3 MPN/g | <3 MPN/g |
| *Escherichia coli* | Absent/g | Absent/g | Absent/g | Absent/g |
| Salmonella | Absent/25 g | Absent/25 g | Absent/25 g | Absent/25 g |

Example 8: Bioavailability Studies

The enhanced bioavailability of curcuminoids presented in the form of collagen peptide-curcuminoid complexes is confirmed by measuring the plasma concentration of curcuminoids over 12 h time period as compared to curcuminoids 95%. Human studies were conducted in accordance with the clinical research guidelines Healthy adult human volunteers (5 males and 3 females; aged between 24 and 46 years), who were not under any medication or dietary supplements were selected for the study. Subjects are assigned with a three digit unique randomization code. Ultraperformance liquid chromatography coupled with electrospray ionization tandem mass spectrometer (UPLC-ESI-MS/MS) (6460 Mass spectrometer, Agilent India Pvt Ltd, Bangalore, India) was employed for the analysis of curcuminoids in plasma or serum or whole blood collected after various post-administration time intervals (0, 1, 3, 5, 8 and 12 h).

Extraction efficiency of curcuminoids from plasma was confirmed by spiking 10 μg/mL of standard solution in 1 mL of blank plasma followed by analysis. Retention time was confirmed by 10 repeated analyses at 20 μg/mL level on the same column under identical conditions. Measurement of the contents in plasma was validated by spiking standard the actives in plasma at 10 and 20 μg/mL concentrations. Extraction efficiency from plasma was 94% with a linear response of R 2 value of 0.998. The identity was established by analytical standards and by multiple reaction monitoring (MRM) of their MS/MS spectra in mass spectrometry.

In a typical protocol followed in the present study, each volunteer was first given one capsule of 500 mg (500 mg×1) of unformulated curcuminoids 95% or Curcuminoid-collagen complex (500 mg of Curcuminoid-collagen complex containing 20% curcuminoids as capsules); blood samples were withdrawn; plasma was separated and frozen at −20° C. till analysis. After 1 week, the subjects were cross-covered and provided with either one capsule of either 500 mg of Curcuminoid-collagen complex containing 20% curcuminoids or unformulated curcuminoid 95%. The protocol of collection of blood and plasma was repeated exactly the same as above. Plasma concentration verses time plot was constructed for the detailed analysis of pharmacokinetics of curcuminoids and their respective formulations to deduce bioavailability or relative absorption.

The same procedure was also repeated with the supplementation of 3 g of collagen-curcuminoids complex containing 8.5% of curcuminoids as a ready-to-drink sachet. Here the powder complex was dissolved in 200 mL of drinking water allowed to drink in such a way that one sachet provides 250 mg of curcuminoids in a soluble form. The blood and plasma samples at various post-administration time points was collected and subjects to LC-MS/MS analysis as before.

Pharmacokinetic parameters like the maximum curcumin concentration in the blood ($C_{max}$), the time taken to reach the maximum concentration ($T_{max}$) and concentration of curcumin in blood after 12 hr ($C^{12}_{max}$) were analysed. It can be seen that the curcuminoids in the new formulation absorbs almost 53 times for in Sachet form and 36 times in capsule form more than the normal curcumin, on an average. Moreover, $T_{max}$ for curcumin-collagen complex was 4.2 hr for Sachet and 7 hr for in capsule administration as compared to the normal curcumin.

Figure 11:
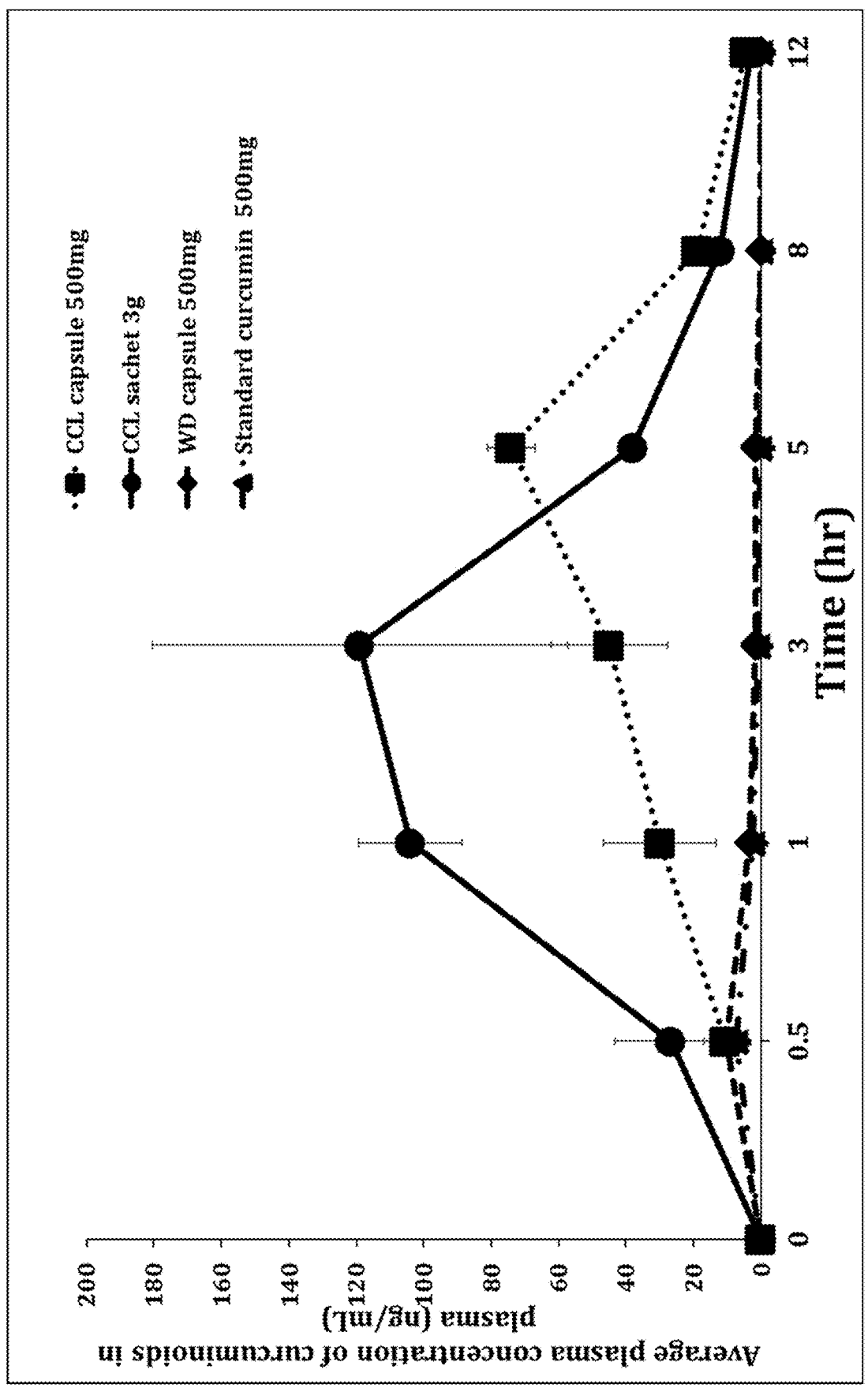
FIG. 11 shows the plasma concentration of curcuminoids when supplemented with unformulated curcumin 95%, water dispersible physical mixture of curcumin and collagen peptides, and curcumin-collagen complex (CCL) in capsule and sachet format.

FIG. 11 shows the plasma concentration verses time graph for curcuminoids when supplemented with curcumin 95%, water dispersible physical mixture of curcumin and collagen peptides, and curcumin-collagen complex in capsule and sachet format. The table 2 provides the pharmacokinetic parameters indicating the higher absorption, bioavailability and longer duration of existence in the blood when curcumin-collagen was consumed as compared to the curcumin alone or its physical mixture with collagen peptides.

TABLE 2

| Sample | Dosage | Cmax (ng/mL) | Tmax (hr) | T½ (hr) | AUC | Folds |
|---|---|---|---|---|---|---|
| CCL Capsule | 500 mg | 74.08 | 5 | 7 | 348.4 | 36.7899 |
| CCL Sachet | 3000 mg | 118.84 | 3 | 4.2 | 506.8 | 53.5164 |
| WD Physical mix* | 500 mg | 10.25 | 0.5 | 0.9 | 16.69 | 1.76241 |
| Standard Curcumin | 500 mg | 4.35 | 0.5 | 0.7 | 9.47 | 1 |

*WD Physical mix—water dispersible physical mixture of curcumin and collagen peptides

Example 9: Cell Permeability of CCL

Figure 12:
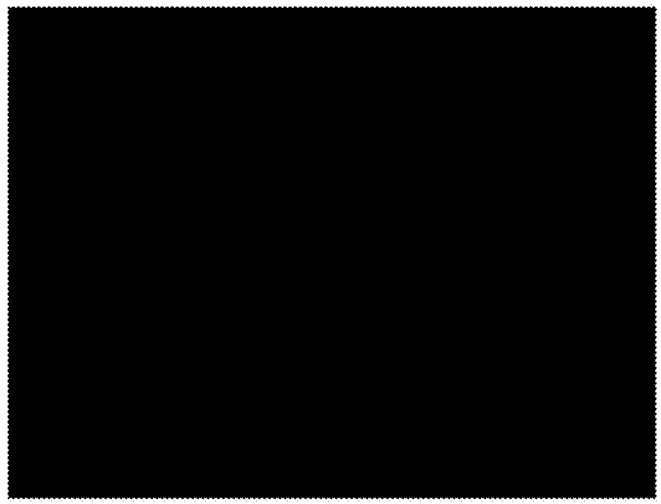
FIG. 12 shows cellular permeability of CCL in comparison with unformulated curcumin 95.
Figure 12:
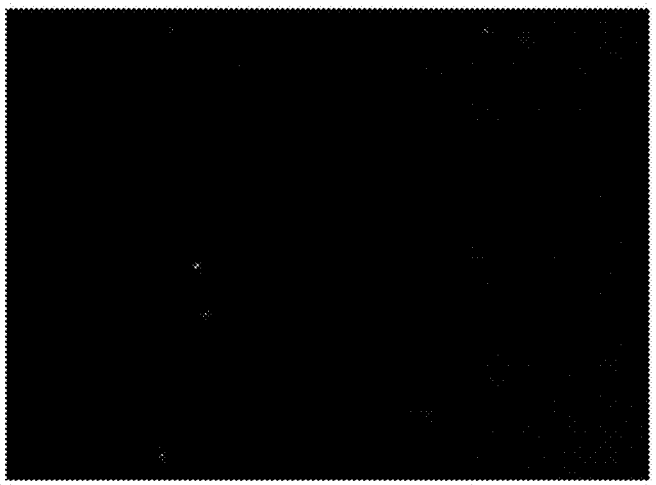
Figure 12:
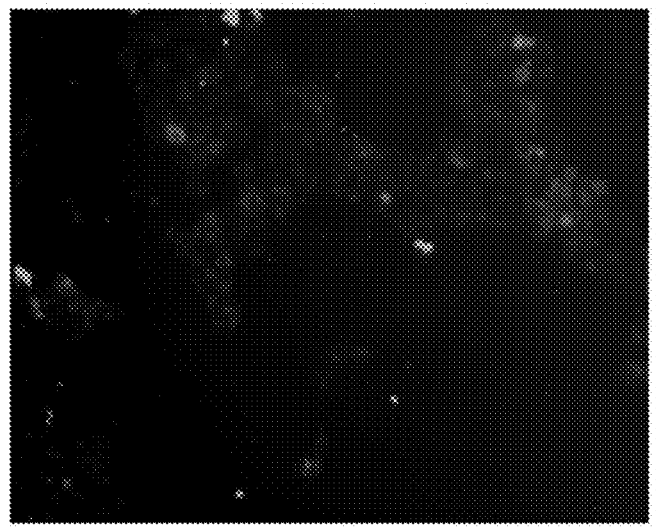

Cell permeability using Inverted Fluorescence Microscope. Fluorescent microscopy was employed to examine the cellular uptake and distribution changes of LFCSNs into HepG2 cells. The HepG2 cells approximately ($1 \times 10^5$) were cultured in a six well plate in a medium made up of EMEM and treated with of LFCSNs for 24 and 48 h with technical triplicates, untreated control and treated cells were observed under inverted microscope. For each experiment, nuclei from 10 random fields of well were examined at 200× magnification (FIG. 12). From the result (FIG. 12), cellular uptake of CCL is clear as compared to C95.

Example 10: Cell Toxicity of CCL

Example 10A: MTT Assay for Cell Proliferation

Figure 13:
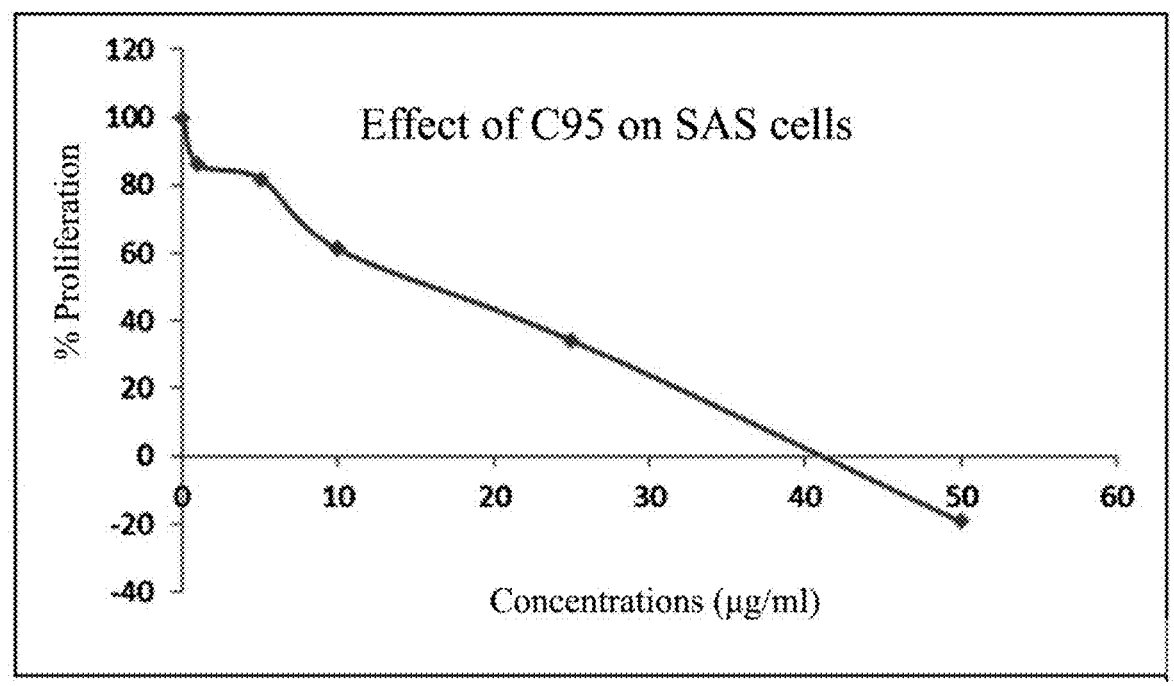
FIG. 13 shows cell proliferation inhibitory effect of CCL in SAS cell lines in comparison with unformulated curcumin 95.
Figure 13:
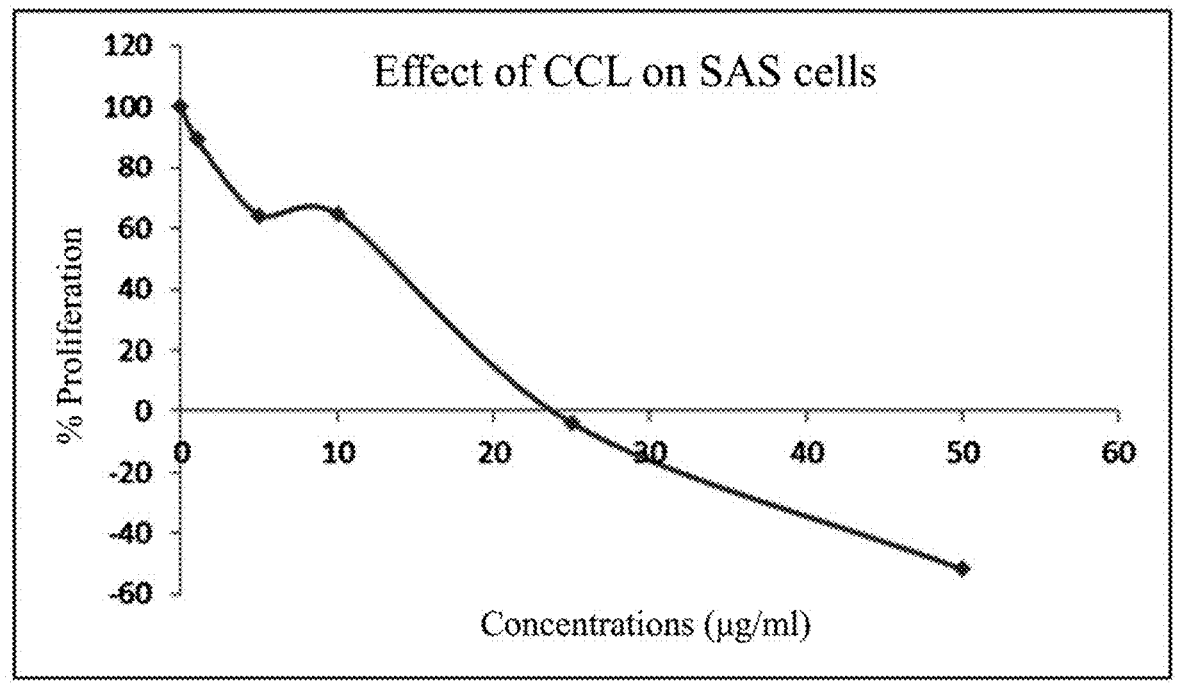

The MTT assay is used to measure cellular metabolic activity as an indicator of cell viability, proliferation and cytotoxicity. This colorimetric assay is based on the reduction of a yellow tetrazolium salt (3-(4,5-dimethylthiazol-2-yl)-2,5-diphenyltetrazolium bromide or MTT) to purple formazan crystals by metabolically active cells. The proliferation study was conducted in SAS cell line. FIG. 13 shows the relative cellular toxicity of CCL in comparison with C95 in SAS cell lines.

Example 10B: Cytotoxicity Assay Using PI FACS

Figure 14A:
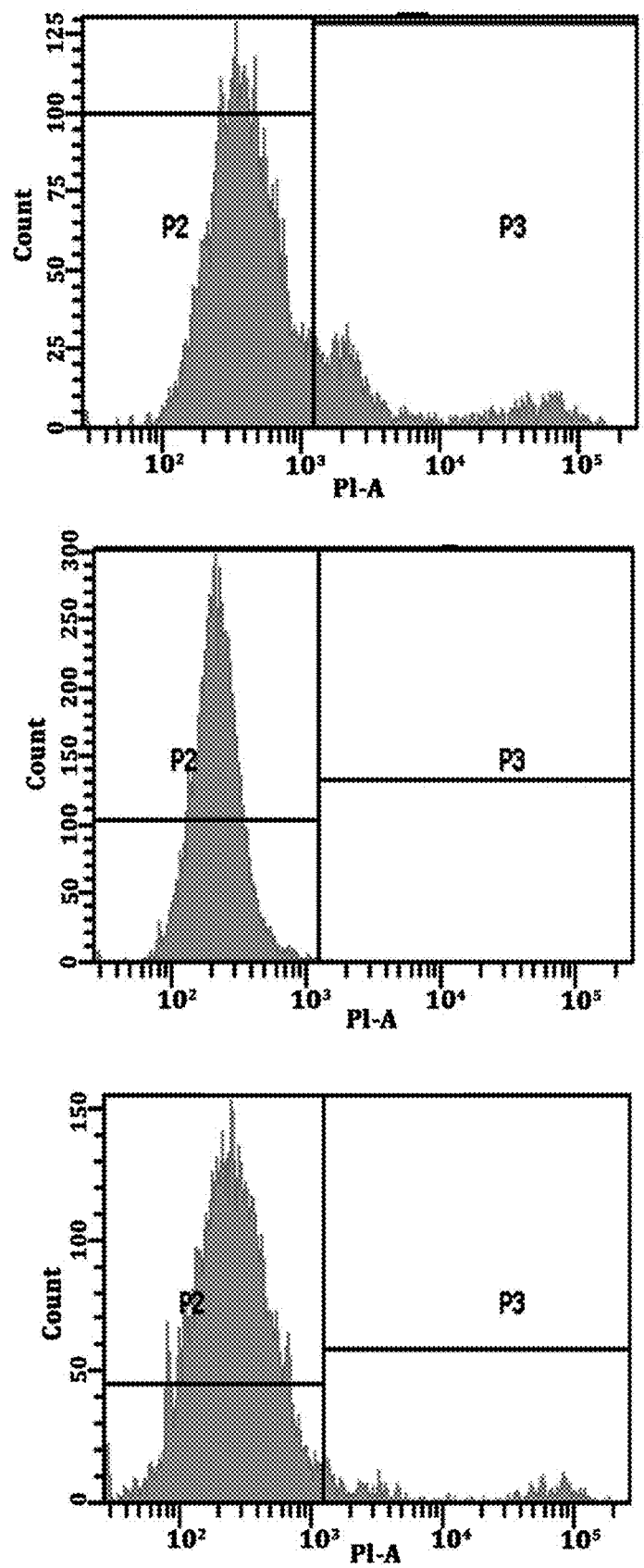
FIG. 14 shows cytotoxicity of CCL investigated by flow cytometry in comparison with unformulated curcumin 95.
Figure 14B:
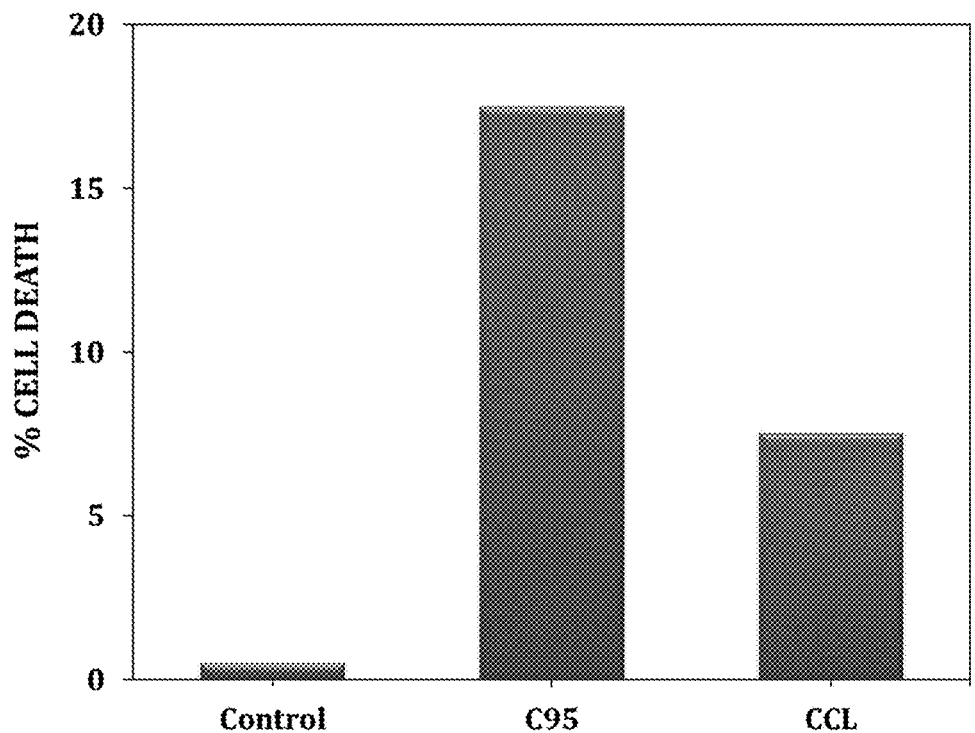

Flow cytometry provides a rapid and reliable method to quantify viable cells in a cell suspension. Live cells have intact membranes that exclude a variety of dyes that easily penetrate the damaged, permeable membranes of non-viable cells. Propidium iodide (PI) is a membrane impermeant dye that is generally excluded from viable cells. It binds to double stranded DNA by intercalating between base pairs. PI is excited at 488 nm and, with a relatively large Stokes shift, emits at a maximum wavelength of 617 nm. In this study 25 ug/mL concentration of C95 in DMSO and CCL in water were used. FIG. 14 shows the flow cytometery data for CCL vs C95.

Example 11: Anti-Inflammatory Effect of CCL

Carrageenan-Induced Mouse Paw Edema Model Male Swiss albino mice were divided into four groups. First group was kept as vehicle control; second group treated with unformulated curcumin at a dose of 50 mg/kg b.wt; third group was treated with CCL at a dose of 50 mg/kg b.wt. Fifth group was treated with standard drug diclofenac at a dose of 25 mg/kg b.wt. The carrageenan-induced mouse hind paw edema test was employed using the method described anteriorly with some modifications. Briefly, after administration for 60 min, each animal except the intact control was injected with 25 μL of 1% freshly prepared carrageenan suspension at the plantar side of right hind paw. The paw edema values were evaluated before as the basal volume ($tC_0$) and 1, 2, 3, 4, 5, or 6 h as the pathological volume ($tC_n$) after carrageenan injection by the MK101CMP paleothermometer (Muromachi Kikai Co., Ltd., Japan). The percentage degree of swelling and inhibition of paw edema were calculated using the following formulas (FIG. 15):

$$\% \text{ inhibition} = \frac{(tC_n - tC_0) - (tT_n - Tt_0) \times 100}{(tC_n - tC_0)}$$

Figure 15:
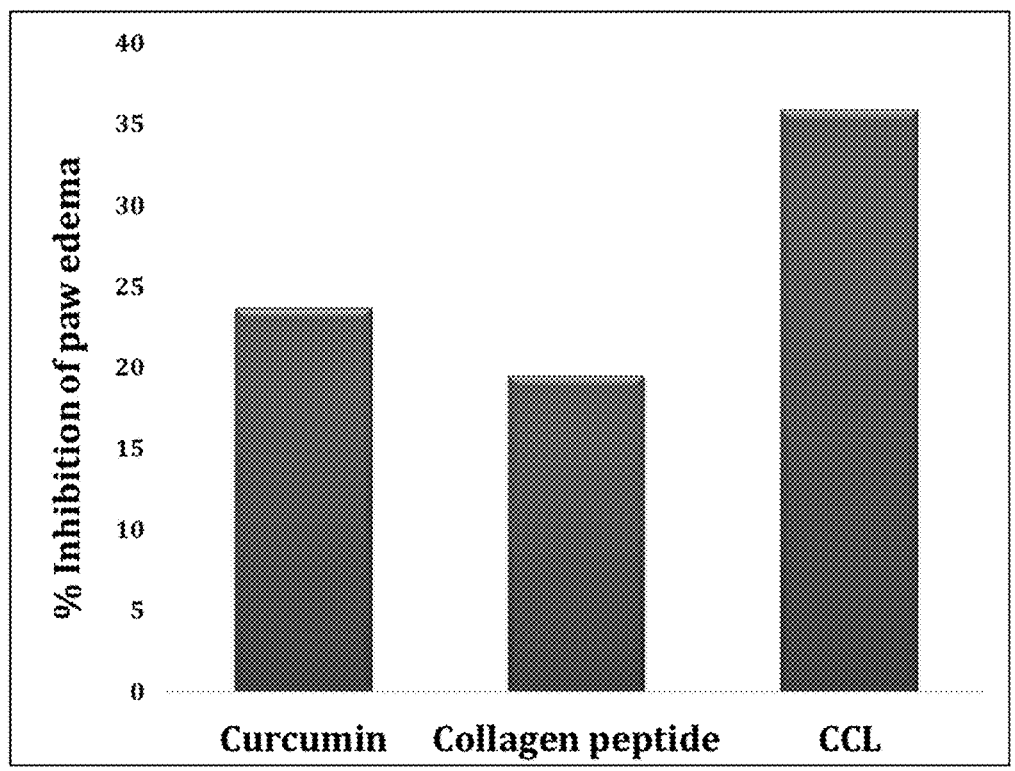
FIG. 15 shows anti-inflammatory effect of CCL in comparison with unformulated curcumin 95.

Where, $tC_n$=paw thickness at particular time point of control animal;
$tC_0$=paw thick ness of control animals before induction;
$tT_n$=paw thickness at particular time point of treated animal; and
$Tt_0$=paw thickness of treated animals before induction It is observed that CCL has offered higher inhibition of paw edema compared to unformulated curcumin and collagen peptide (FIG. 15).

Example 12

Delivery forms comprising collagen peptide-curcuminoid complex compositions comprising the collagen peptide-curcuminoid complexes formulated as capsules, tablets, soft-gels, powders, ready-to-consume mixes, granules, liquids for consumption as such, in aqueous beverages, incorporated in dairy products, candies like gummies, milk powder, protein shakes etc., demonstrated the stability and increased bioavailability of various dosage forms at 100 to 500 mg/serving.

The invention claimed is:
1. A method of preparing water soluble pharmaceutical composition, comprising the steps of:
    a. micronising hydrophobic bioactive molecules to form micronized hydrophobic bioactive molecules;
    b. emulsifying the micronized hydrophobic bioactive molecules by homogenisation with an emulsifier with phosphatidylcholines to form emulsified hydrophobic bioactive molecules;
    c. dissolving collagen peptides in water at a concentration range of 20 to 95% to form dissolved collagen peptides;
    d. sonicating the emulsified hydrophobic bioactive molecules from step (b) with the dissolved collagen peptides from step (c) to form a complex of hydrophobic bioactive molecules;
    e. encapsulating the complex from step (d) by ultrasound mediated homogenisation to form encapsulated complex of hydrophobic bioactive molecules; and
    f. drying the encapsulated complex from step (e) by spray drying or freeze drying to form the water soluble pharmaceutical composition;
    wherein said collagen peptides form an amorphous, nano-sized non-covalent complex with the hydrophobic bioactive molecules and encapsulated in the collagen peptide matrix, and wherein the hydrophobic bioactive molecules are selected from the group consisting of curcuminoids, gingerol, flavonoids, stilbenes, carotenoids, terpenes, terpenoids, and chlorophyll.

2. The method of claim 1, wherein the emulsifier is lecithin.

3. A water soluble pharmaceutical composition prepared by the method of claim 1.

4. A water soluble pharmaceutical composition of claim 3, wherein the hydrophobic bioactive molecules are present at a concentration in the range of from 1 to 25% of the composition.

5. The water soluble pharmaceutical composition of claim 3, wherein the collagen peptides are present at a concentration in the range of from 10 to 90% of the composition.

6. The water soluble pharmaceutical composition of claim 3, wherein the hydrophobic bioactive molecules exhibit enhanced solubility and stability as compared to unformulated hydrophobic bioactive molecules.

7. The water soluble pharmaceutical composition of claim 3, wherein the hydrophobic bioactive molecules exhibit an increased bioavailability, increased absorption and a longer half-life following an oral administration to a subject, as compared to unformulated hydrophobic bioactive molecules.

8. The water soluble pharmaceutical composition of claim 3, wherein the hydrophobic bioactive molecules exhibit an increased cellular permeability, as compared to unformulated hydrophobic bioactive molecules.

9. The water soluble pharmaceutical composition of claim 3, wherein the water soluble pharmaceutical composition exhibits an enhanced anti-inflammatory effect following an oral administration to a subject, as compared to unformulated hydrophobic bioactive molecules.

10. The water soluble pharmaceutical composition of claim 3, wherein the water soluble pharmaceutical composition is prepared for oral administration in a form of capsules, tablets, softgels, beadlets, liquid solution, liquid suspension, liquid emulsion, or powder sachets for enhanced bioavailability of the hydrophobic bioactive molecules.

11. The water soluble pharmaceutical composition of claim 3, wherein the water soluble pharmaceutical composition is prepared for oral administration at a dose of from 100 to 500 mg/dose in the form of tablets, capsules or softgel.

12. The water soluble pharmaceutical composition of claim 3, wherein the water soluble pharmaceutical composition is prepared for oral administration at a dose of 1000 mg to 5000 mg per sachet, once or twice a day, to deliver a minimum of 100 mg to 500 mg of hydrophobic bioactive molecules and 1 g to 10 g of collagen peptides/dosage/day.

* * * * *